US012651663B2

(12) United States Patent
Di Genova

(10) Patent No.: US 12,651,663 B2
(45) Date of Patent: Jun. 9, 2026

(54) PHARMACEUTICAL ORDER PROCESSING SYSTEMS AND METHODS

(71) Applicant: Express Scripts Strategic Development, Inc., St. Louis, MO (US)

(72) Inventor: Gabriel Di Genova, Wildwood, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 640 days.

(21) Appl. No.: 17/975,376

(22) Filed: Oct. 27, 2022

(65) Prior Publication Data

US 2023/0133785 A1 May 4, 2023

Related U.S. Application Data

(60) Provisional application No. 63/272,925, filed on Oct. 28, 2021.

(51) Int. Cl.
| | |
|---|---|
| *B65B 5/12* | (2006.01) |
| *B65B 61/22* | (2006.01) |
| *G16H 20/10* | (2018.01) |
| *G16H 40/20* | (2018.01) |

(52) U.S. Cl.
CPC .............. *G16H 40/20* (2018.01); *B65B 5/12* (2013.01); *G16H 20/10* (2018.01)

(58) Field of Classification Search
None
See application file for complete search history.

(56) References Cited

U.S. PATENT DOCUMENTS

| | | | |
|---|---|---|---|
| 6,781,522 | B2 | 8/2004 | Sleva |
| 6,913,056 | B2 | 7/2005 | Landherr |
| 7,006,530 | B2 | 2/2006 | Spinar |
| 7,459,054 | B2 | 12/2008 | Landherr |
| 7,507,705 | B2 | 3/2009 | Buschmann |
| 8,146,642 | B2 | 4/2012 | Landherr |
| 8,263,650 | B2 | 9/2012 | Cook |
| 8,281,312 | B2 | 10/2012 | Gnanasambandam |
| 8,417,550 | B2 | 4/2013 | Gabrielson |
| 8,521,327 | B2 | 8/2013 | Pinney |

(Continued)

FOREIGN PATENT DOCUMENTS

| | | | | |
|---|---|---|---|---|
| CN | 109606786 A | * | 4/2019 | .............. B65B 21/04 |
| CN | 109606819 A | * | 4/2019 | .............. B65B 5/105 |
| KR | 20160089206 A | * | 7/2016 | ........... B65B 43/265 |

*Primary Examiner* — Tanzim Imam
(74) *Attorney, Agent, or Firm* — Stinson LLP

(57) ABSTRACT

A pharmaceutical order processing system, components thereof, and associated methods for filling a prescription order. The pharmaceutical order processing system includes a lower insert placer, a syringe placer, a dosing cup placer, a pharmaceutical container placer, and/or an upper insert placer. The lower insert placer places a lower insert into a box. The syringe placer places a syringe into a syringe compartment of the lower insert. The dosing cup placer places a dosing cup into a dosing cup compartment of the lower insert. The pharmaceutical container placer places a pharmaceutical container into a pharmaceutical container compartment of the lower insert. The upper insert placer places an upper insert into the box after the box has received the lower insert and the lower insert has received the syringe, the dosing cup and the pharmaceutical container.

20 Claims, 22 Drawing Sheets

(56) References Cited

U.S. PATENT DOCUMENTS

| | | | |
|---|---|---|---|
| 9,125,089 B2 | 9/2015 | Gopalasetty | |
| 9,150,119 B2 | 10/2015 | Henderson | |
| 9,179,321 B2 | 11/2015 | Hasarchi | |
| 9,220,154 B2 | 12/2015 | Dingemans | |
| 9,238,558 B2 | 1/2016 | Houck | |
| 9,271,896 B2 | 3/2016 | Clements | |
| 9,280,157 B2 | 3/2016 | Wurman | |
| 9,286,590 B2 | 3/2016 | Segawa | |
| 9,373,065 B1 | 6/2016 | Hoffman | |
| 9,409,201 B2 | 8/2016 | Summons | |
| 9,575,273 B2 | 2/2017 | Cabanne Lopez | |
| 9,586,008 B2 | 3/2017 | Shetty | |
| 9,592,343 B2 | 3/2017 | Shetty | |
| 9,597,454 B2 | 3/2017 | Wetzel | |
| 9,639,245 B2 | 5/2017 | Sang | |
| 9,649,303 B2 | 5/2017 | Penn | |
| 9,665,688 B2 | 5/2017 | Terzini | |
| 9,681,772 B2 | 6/2017 | Atilla | |
| 9,694,977 B2 | 7/2017 | Aprea | |
| 9,697,335 B2 | 7/2017 | Joplin | |
| 9,913,147 B2 | 3/2018 | Brighenti | |
| 9,944,419 B2 | 4/2018 | Joplin | |
| 9,978,036 B1 | 5/2018 | Eller | |
| 10,053,248 B2 | 8/2018 | Joplin | |
| 10,303,854 B2 | 5/2019 | Joplin | |
| 10,356,664 B2 | 7/2019 | Pascal | |
| 10,492,223 B2 | 11/2019 | Lee | |
| 10,589,931 B2 | 3/2020 | Jarvis | |
| 10,660,734 B1 * | 5/2020 | Chapman | B65B 23/00 |
| 10,674,538 B2 | 6/2020 | Li | |
| 10,702,451 B2 | 7/2020 | Lum | |
| 10,782,670 B2 | 9/2020 | Crivella | |
| 10,832,209 B2 | 11/2020 | Rajkhowa | |
| 10,850,926 B2 | 12/2020 | Greyshock | |
| 2007/0198347 A1 | 8/2007 | Muldoon | |
| 2011/0106673 A1 | 5/2011 | Shanley | |
| 2013/0173489 A1 | 7/2013 | Gabrielson | |
| 2015/0073052 A1 | 3/2015 | Cook | |
| 2016/0151246 A1 | 6/2016 | Sotelo | |
| 2018/0180429 A1 | 6/2018 | De Lorenzo | |
| 2019/0214120 A1 * | 7/2019 | Hoffman | G06Q 10/087 |
| 2023/0126344 A1 | 4/2023 | Swindells | |
| 2023/0130332 A1 | 4/2023 | Swindells | |
| 2023/0136001 A1 | 5/2023 | Di Genova | |
| 2023/0139860 A1 | 5/2023 | Di Genova | |

* cited by examiner

PHARMACEUTICAL ORDER PROCESSING SYSTEMS AND METHODS

CROSS-REFERENCE TO RELATED APPLICATION

The present application claims priority to U.S. Provisional Application No. 63/272,925, filed on Oct. 28, 2021, the entirety of which is hereby incorporated by reference.

FIELD

The present disclosure generally relates to pharmaceutical processing systems, and more particularly to pharmaceutical order processing systems for processing pharmaceutical containers, syringes and dosing cups.

BACKGROUND

High volume pharmacies process and fulfill a large number of prescription orders per day. These pharmacies often rely on automated systems to process, fill, and pack one or more prescriptions together for delivery to a patient. These automated systems generally fit into one of two categories: (1) systems, such as high-volume fillers, that automatically fill pharmaceutical containers (e.g., auto-filled containers) with specific quantities of pharmaceuticals; and (2) systems, such as unit-of-use systems, that process unit-of-use products or containers. A unit-of-use container contains an entire prescription of a pharmaceutical and can therefore be sent to the patient without modifying the pharmaceutical(s) (e.g., the quantity, type, etc.) in the container and without product packaging modification (or with minimal product packaging modification) except for labeling with patient information. Unit-of-use products can include a full course of medicine to be taken by a patient, for example, an entire prescription (e.g., a thirty-day supply, a sixty-day supply, or a ninety-day supply). The unit-of-use products contain known quantities of medication in packages that are closed and sealed by, for example, the pharmaceutical manufacturer.

SUMMARY

In one aspect, a pharmaceutical order processing system for filling a prescription order is disclosed. The pharmaceutical order processing system comprises a lower insert placer configured to place a lower insert into a box. At least one ancillary placer is provided to place equipment (e.g., a syringe, a cup, sanitizer or the like) to be used with the main item (e.g., a drug) being filled in an order within the box. A syringe placer is configured to place a syringe into a syringe compartment of the lower insert. A dosing cup placer is configured to place a dosing cup into a dosing cup compartment of the lower insert. A pharmaceutical container placer is configured to place a pharmaceutical container into a pharmaceutical container compartment of the lower insert. An upper insert placer is configured to place an upper insert into the box after the box has received the lower insert and the lower insert has received the ancillaries and the main item, e.g., the syringe, the dosing cup and the pharmaceutical container.

In another aspect, a method of processing a pharmaceutical order comprises inserting a lower insert into a box; placing a syringe into a syringe compartment of the lower insert; placing a dosing cup into a dosing cup compartment of the lower insert; placing a pharmaceutical container into a pharmaceutical container compartment of the lower insert;

and inserting an upper insert into the box after the box has received the lower insert and the lower insert has received the syringe, the dosing cup and the pharmaceutical container.

In another aspect, an insert placer for placing an insert into a box comprises an insert transporter configured to move the insert into a box. An insert supplier is configured to supply the insert to the insert transporter. The insert supplier includes an insert receiver and a lift. The insert receiver has an interior sized and shaped to receive and hold a stack of inserts. The insert receiver has an upper removal location from which the insert is removed from the insert receiver by the insert transporter. The lift is configured to raise the stack of inserts disposed in the interior of the insert receiver upward to move an upper-most insert in the stack of inserts to the removal location.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
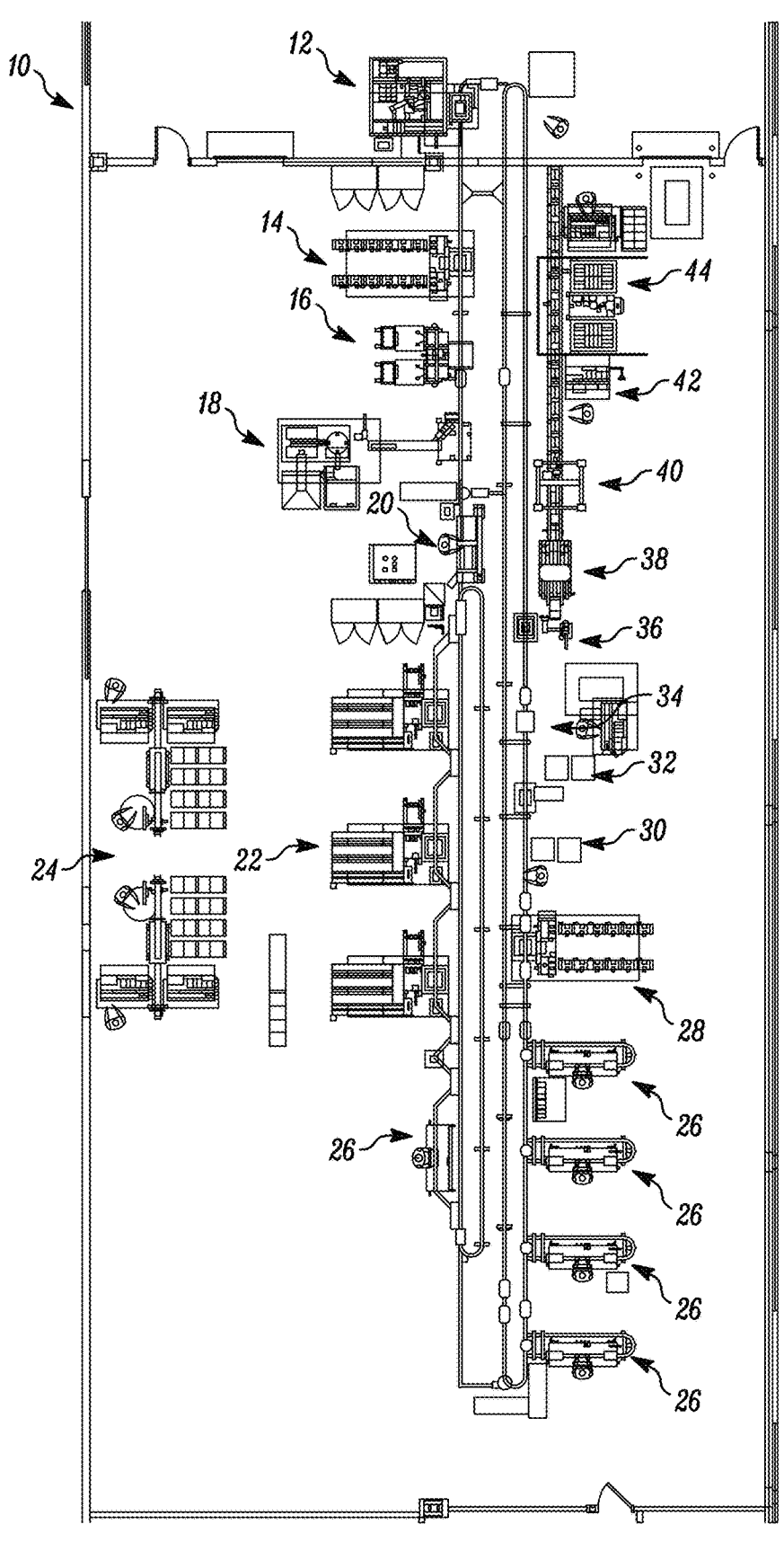
FIG. 1 is a plan view of a pharmaceutical order processing system according to one embodiment of the present disclosure.
Figure 2:
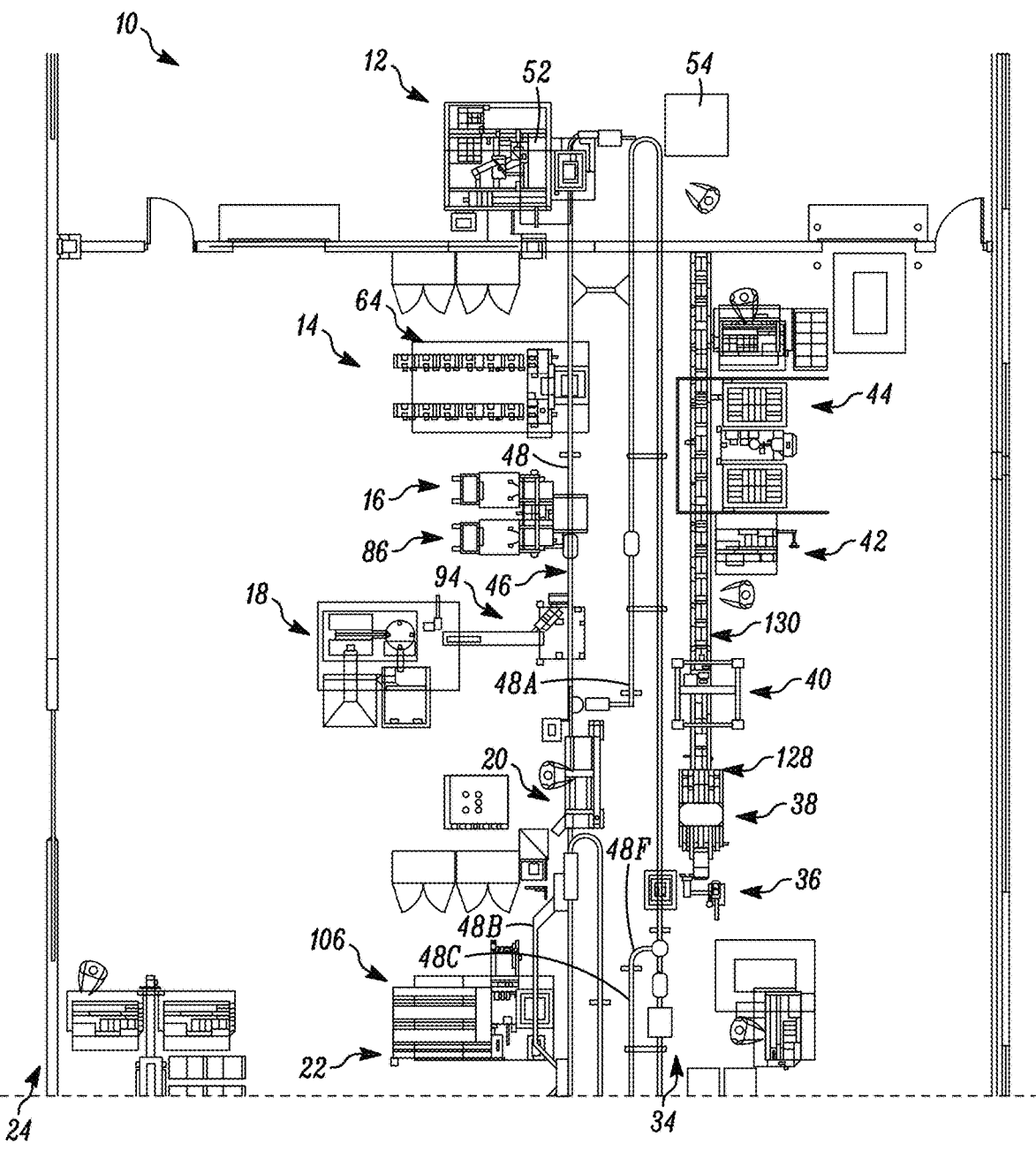
FIG. 2 is an enlarged, fragmentary plan view of a portion of the pharmaceutical order processing system of FIG. 1.
Figure 3:
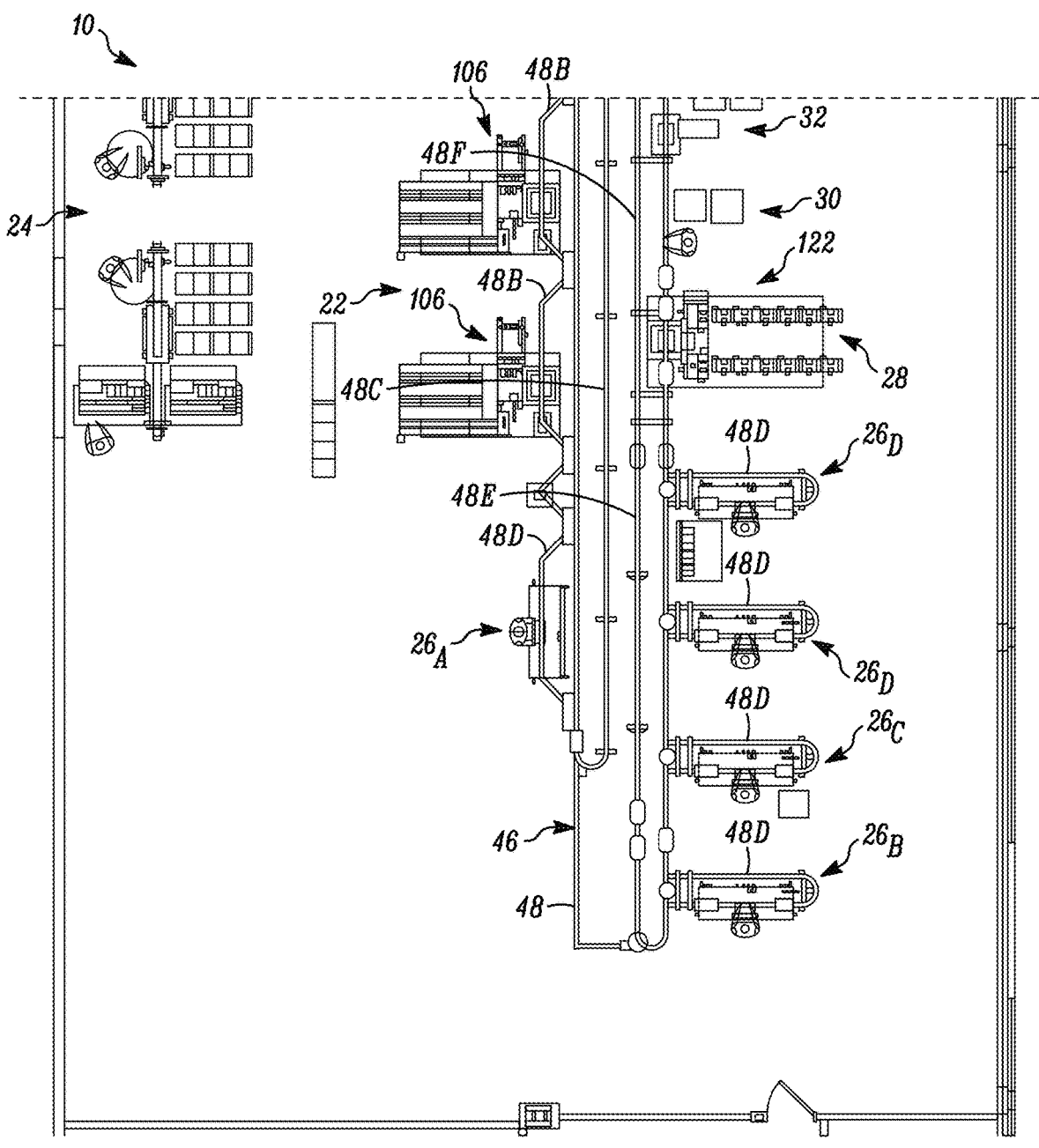
FIG. 3 is an enlarged, fragmentary plan view of another portion of the pharmaceutical order processing system of FIG. 1.
Figure 4:
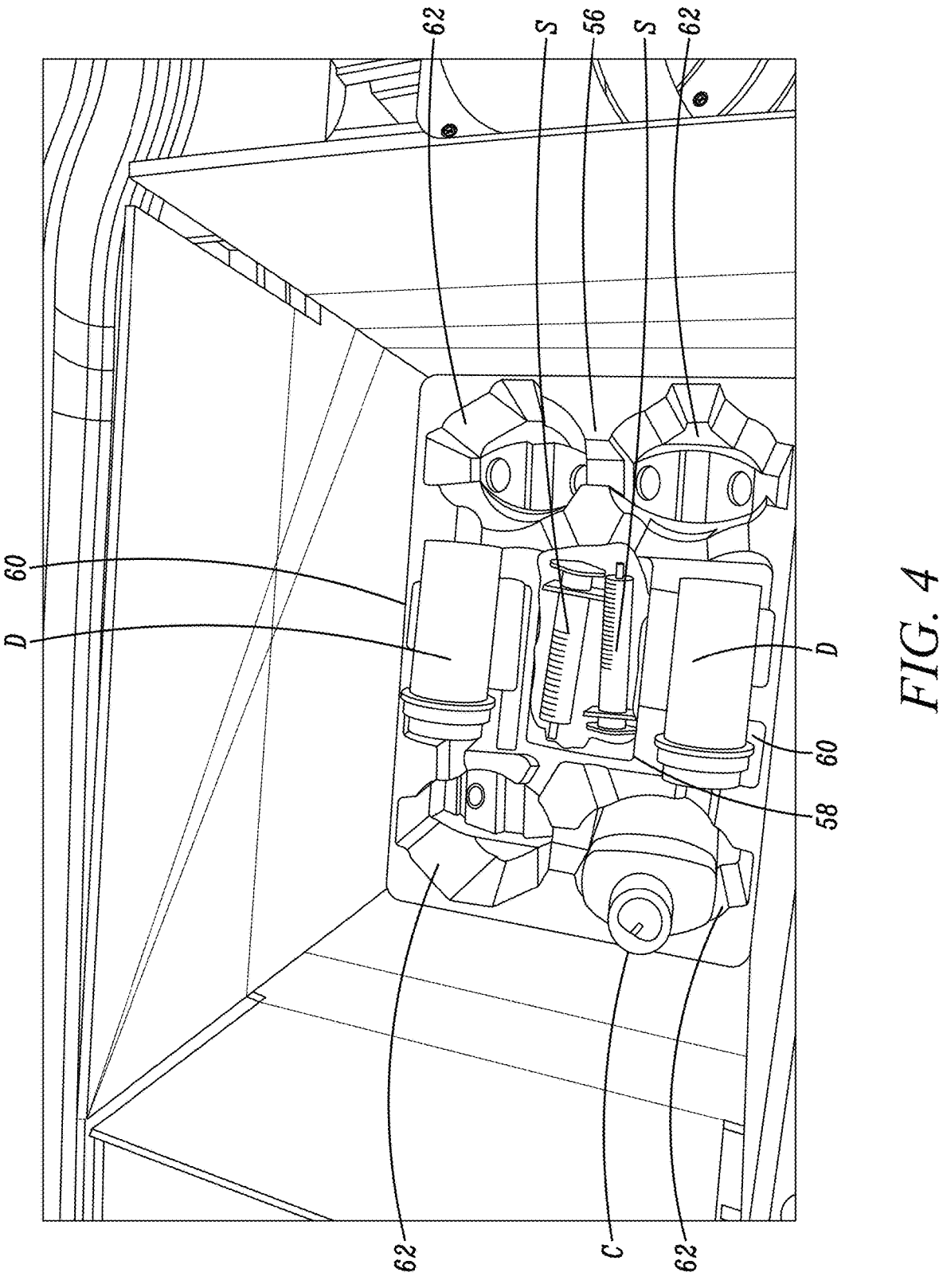
FIG. 4 is a perspective of a box filled by the pharmaceutical order processing system.
Figure 5:
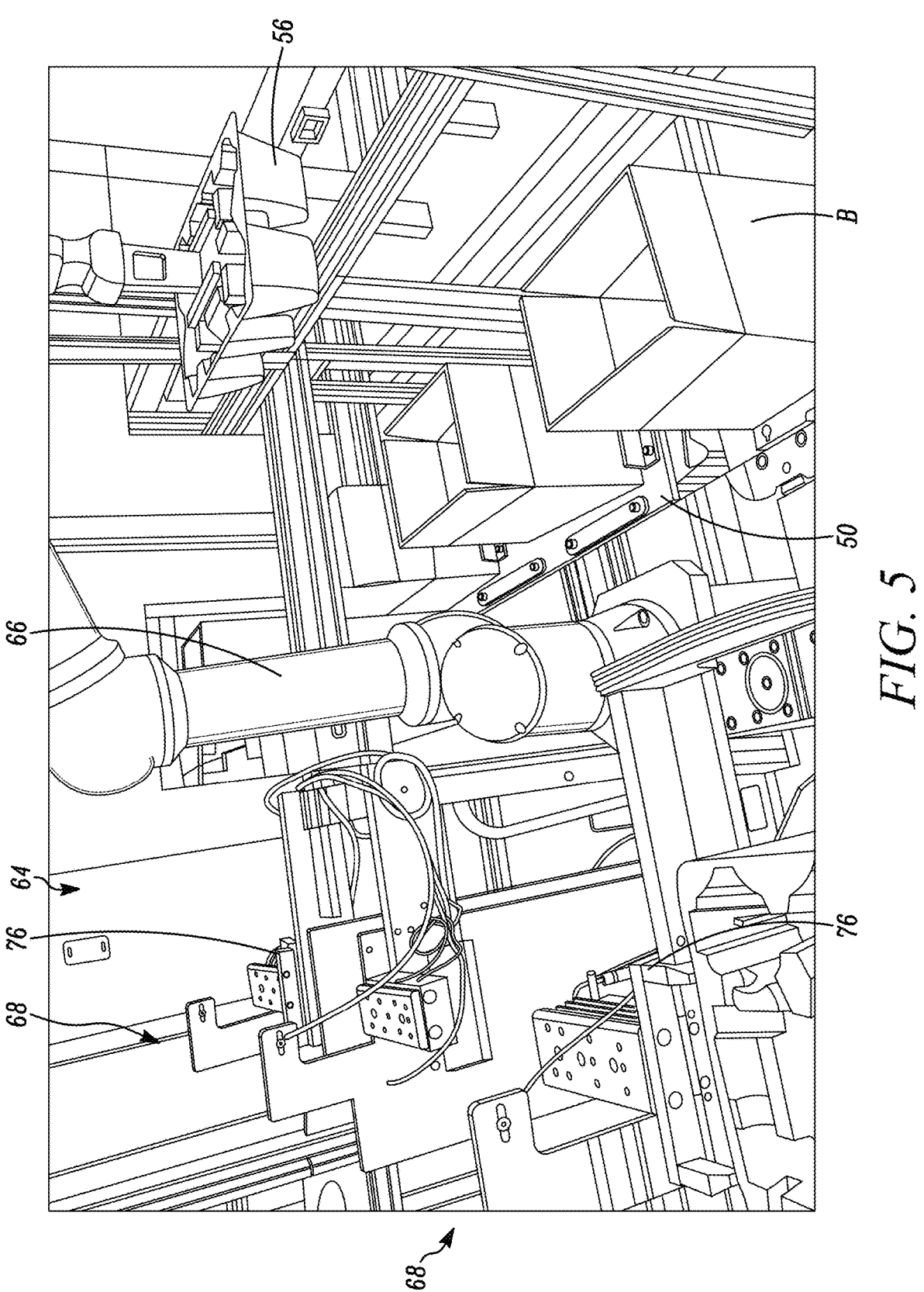
FIG. 5 is a perspective of a lower insert placer of the pharmaceutical order processing system.

Referring to FIGS. 1-3, a pharmaceutical order processing system ("system") according to one embodiment of the present disclosure is generally indicated at 10. The system 10 processes prescription orders received by the system. A prescription order may include one or more pharmaceuticals (e.g., prescription drugs), which are contained in pharmaceutical containers C (FIG. 4). The illustrated pharmaceutical containers C are in the form of bottles, although it is understood the pharmaceutical containers may have other forms such as a box or any other suitable container. The pharmaceutical order processing system 10 comprises a unit-of-use system that processes pharmaceutical containers C that are generally unit-of-use products. The pharmaceutical order processing system 10 generally stores, monitors, labels, dispenses and packages the unit-of-use pharmaceutical containers C. The system 10 also packages syringes S and dosing cups D with the pharmaceutical containers C in a box or package B (FIG. 4). In the illustrated embodiment, the system 10 processes liquid pharmaceuticals. When a patient takes the liquid pharmaceutical, the patient measures an amount of the liquid pharmaceutical using the syringe S and generally dilutes the amount with another liquid, such as water, in the dosing cup D. It is understood the pharmaceutical order processing system 10 may also be used with non-unit-of-use systems, such as a high-volume pharmaceutical order processing system (e.g., a high-volume filler). Further details on pharmaceutical order processing systems and components thereof, including unit-of-use systems, may be found in U.S. Pat. Nos. 9,373,065, 9,697,335, 9,944,419, 9,978,036, and 10,053,248, the entireties of which are hereby incorporated by reference. However, it will be appreciated that the systems and components disclosed herein can be used in other contexts without departing from the scope of the present disclosure.

The system 10 processes the syringes S, the dosing cups D and the pharmaceutical containers C to fill prescription orders. To process the prescription order, the system 10 includes a set of operation stations (described in more detail below) along which a set of processing operations occur. Broadly, a station is where one or more operations (e.g., functions) occur to further the processing or fulfilment of the prescription order and generally include the one or more components that perform the one or more operations (i.e., the one or more components are at the station). One or more operations may occur at each station. In the illustrated embodiment, the system 10 includes a box erector station 12, a lower insert station 14, a syringe station 16, a dosing cup station 18, a box check station 20, a pharmaceutical container station 22, a filling station 24, a manual station 26, an upper insert station 28, a manual paper insert station 30, an automatic paper insert station 32, a weighing station 34, an unloading station 36, a box closing station 38, a shipping label station 40, a shipping label verification station 42, and collection station 44. The system 10 may include one or more of each type of station. Also, stations can be omitted entirely. The system 10 may also include other types of stations as well. As will become apparent, the system 10 processes and fulfills a prescription order using the stations. The system 10 is generally an automated system used to auto process received prescription orders. The general movement between the stations is described in more detail below, although other paths of movements between the stations are within the scope of the present disclosure.

Figure 21:
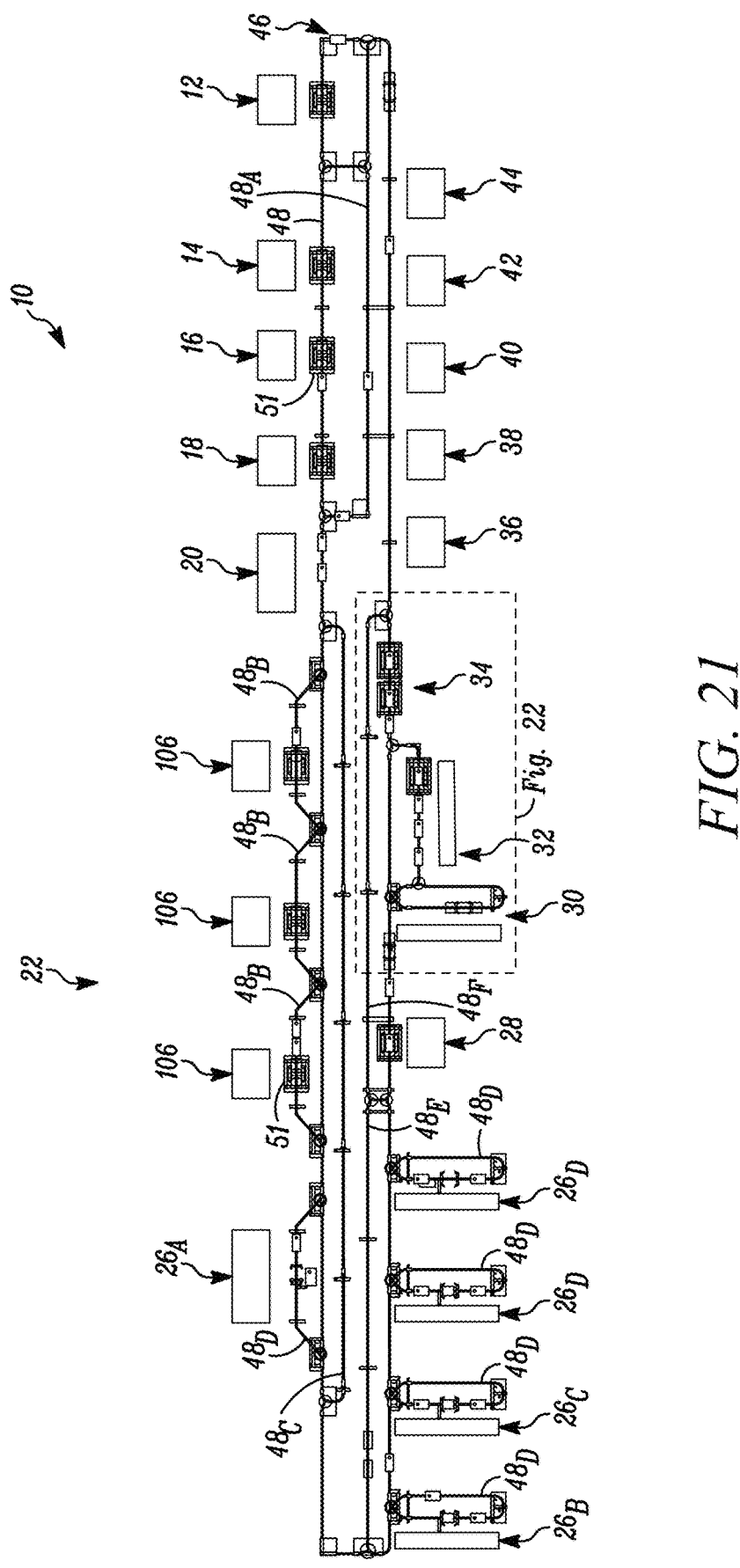
FIG. 21 is a plan view of a pharmaceutical order processing system according to another embodiment of the present disclosure.
Figure 22:
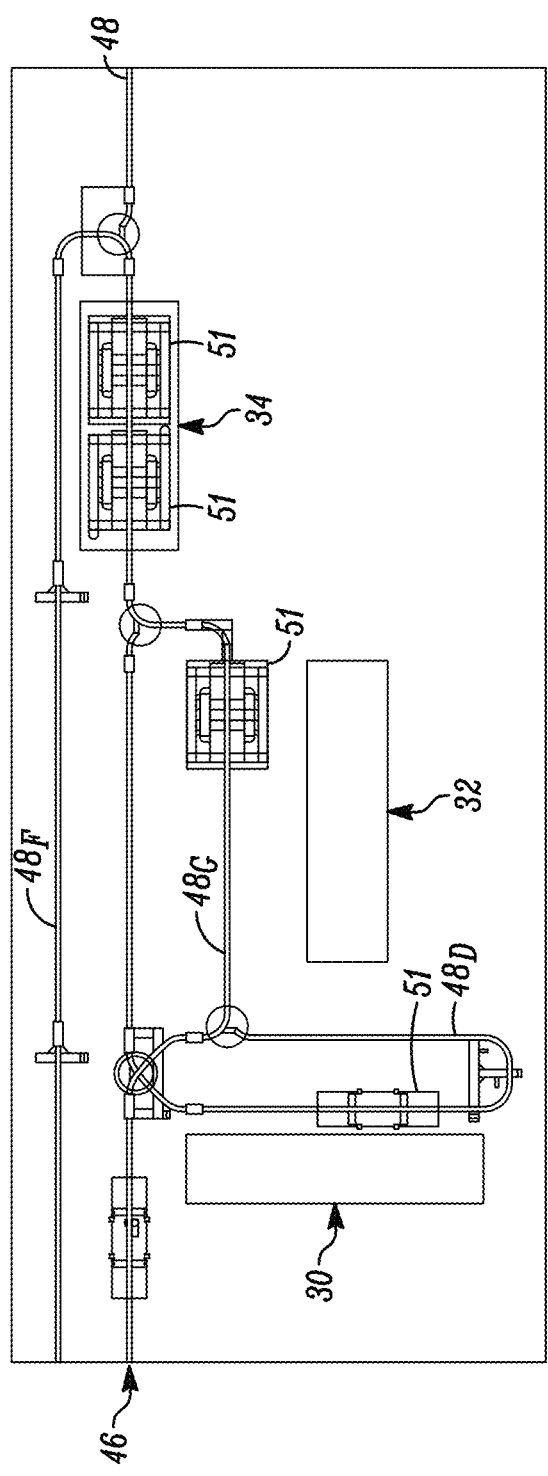
FIG. 22 is an enlarged, fragmentary plan view of a portion of the pharmaceutical order processing system of FIG. 21.

The system 10 includes a conveyor 46. The conveyor 46 includes a pathway or track 48 (e.g., mono-rail) and one or more carriers or carriages 50 (e.g., box carriers or carriages) movable along the pathway. The pathway 48 generally travels between the stations (e.g., the stations are positioned along the pathway). Each carriage 50 is configured to support and move a box B along the pathway 48 to the different stations. The pathway 48 forms a closed loop, allowing the carriages 50 to repeatedly move to different stations along the pathway. As will come apparent, the carriages 50 travel in as single direction (e.g., a generally counter-clockwise direction) along the pathway 48. The pathway 48 may include one or more positioning units or carriage holders 51 (see FIGS. 19, 21, and 22) at each station (broadly, each station includes one or more carriage holders) for holding the carriages 50 in position at the stations while the various different processing operations are performed. The pathway 48 includes a main path and one or more branch paths (described in more detail below). The main path of the pathway 48 forms the closed loop. The pathway 48 includes switches that connect the branch paths to the main path and can be selectively actuated to direct the carriages onto/off of a branch path or to bypass a branch path. In one embodiment, each carriage 50 includes a mover, such one or more wheels connected to an electric motor, which moves the carriage 50 around the pathway 48. Thus, each carriage 50 is independently moveable along the pathway 48. Each carriage 50 may include an identification tag (not shown), such as an RFID tag or a machine-readable tag. The identification tag can contain an identifier (such as a carriage number or an order number) to associate the identifier with the particular carriage 50. Some of the stations may include communication modules or scanners, such as RFID scanners, which are used to acquire the identifier from the identification tag.

Still referring to FIGS. 1 and 2, the box erector station 12 of the system 10 erects the boxes B. The box erector station 12 may include an automated box erector 52 that automatically erects the boxes B (e.g., cardboard boxes) from generally flat box blanks. The box erector station 12 may also include a table 54 for the manual construction of the boxes B. Preferably, the box erector station 12 is in a different room than the rest of the stations, as shown, to prevent cardboard dust from the boxes B from reaching the other stations. In the illustrated embodiment, the box erector station 12 is in one room and the other stations are in a separate room. Each room can have a separate environment control system to control the environment and filter the air therein. At the box erector station, empty carriages 50 receive the erected boxes B. The erected boxes B are still open at the top to allow the different elements (e.g., order components) to be inserted or placed into the boxes. In one embodiment, the identifier of the identification tag of the carriage 50 is set at the box erector station. Preferably, the system 10 also includes a box ID applier (not shown) configured to apply a machine-readable marking on the box B. The box ID applier may be at the box erector station 12. The machine-readable marking (e.g., a barcode, 2D code, QR code, alphanumeric code, etc.) generally represents an identifier associated with a prescription order (such as the order number) received by the system 10. The identifier may also be used to identify the box B. The identifier represented by the machine-readable marking may be the same or different from the identifier in the identification tag on the carriage 50. Some of the stations may include scanners, such as barcode scanners, that are used to acquire the identifier from the machine-readable marking. Some of the stations may initiate processes or tasks based on the acquisition of the identifier from the box B and/or carriage 50. After the box B is loaded onto its corresponding carriage 50, the carriage travels (downstream) along the pathway 48 to move the box to the lower insert station 14.

At the lower insert station 14, a lower insert 56 (e.g., lower box insert) is inserted into to box B. The lower insert 56 includes a plurality of compartments to receive a main item and ancillary items. The lower insert 56 (broadly, an order component receiver or holder) includes one or more syringe compartments 58 for receiving the syringes S, one or more dosing cup compartments 60 for receiving the dosing cups D and one or more pharmaceutical container compartments 62 for receiving the pharmaceutical containers C (FIG. 4). Generally, each compartment 58, 60, 62 is sized and shaped to correspond to the order component (e.g., syringes S, dosing cups D, pharmaceutical containers C) the respective compartments receive, support and hold.

Referring to FIGS. 5-9, the lower insert station 14 includes a lower insert placer 64 (e.g., an insert loader). The lower insert placer 64 is configured to place a lower insert 56 into the box B (when the carriage 50 carrying the box is at the lower insert station 14). The lower insert placer 64 includes an insert transporter 66 configured to move the lower insert 56 into the box B. Specifically, the insert transporter 66 is configured to pick up and remove an insert 56 from a stack and place the insert in the box B. In the illustrated embodiment, the insert transporter 66 comprises a robot such as a six-axis robotic arm, although other robots are within the scope of the present disclosure. For example, the insert transporter 66 may comprise a selective-compliance-articulated robotic arm, a cylindrical robot, a delta robot, a polar coordinate robot, a vertically articulated robot, a Cartesian coordinate robot or any other suitable device. The insert transporter 66 includes a lower insert grabber (broadly, end-of-arm tooling) configured to selectively grab a lower insert 56 to move the lower insert.

The lower insert placer 64 includes at least one insert supplier 68. In the illustrated embodiment, the lower insert placer 64 includes two insert suppliers 68, one on each side of the insert transporter 66. This provides redundancy, enabling the lower insert placer 64 to still be able to place the lower inserts 56 into boxes B even if one of the insert suppliers 68 stops working. The two insert suppliers 68 are generally identical, accordingly, one insert supplier will now be described with the understanding the description applies to both insert suppliers.

The insert supplier 68 is configured to supply the lower inserts 56 to the insert transporter 66. The insert transporter 66 removes the lower inserts 56, one at a time, from the insert supplier 68 to place each lower inserts into one of the boxes B. The insert supplier includes an insert receiver 70 and a lift 72. The insert receiver 70 has (e.g., defines) an interior sized and shaped to receive and hold a stack 74 of lower inserts 56. The insert receiver 70 has a rear wall and opposite side walls that define the interior. The front the interior is open to permit a stack 74 of lower inserts to be moved into the interior. The interior of the insert receiver 70 has a generally rectangular cross-sectional shape to match the shape of the lower inserts 56. The insert receiver 70 includes (e.g., defines) a removal location adjacent (e.g., at) an upper end of the insert receiver. The removal location is the location from which the lower inserts 56 are removed from the insert receiver 70 by the insert transporter 66. Specifically, the insert transporter 66 grabs the lower insert 56 at the removal location and removes (e.g., picks up) the lower insert from the stack 74 and insert receiver 70. The lift 72 moves the stack 74 of lower inserts 56 upward so that the upper-most lower insert 56 (e.g., the insert at the top of the stack) is disposed at the removal location. In particular, the lift 72 supports the stack 74 of lower inserts 56 and moves upward to move the lower inserts toward the removal location. The lift 72 moves the stack 74 of lower inserts 56 upward after the upper-most lower insert is removed by the insert transporter 66 to move the subsequent upper-most lower insert (now the upper-most lower insert) to the removal location, thereby positioning the subsequent upper-most lower insert at the removal location to be grabbed by the insert transporter. This process repeats (e.g., the lift 72 continues to rise) as the lower inserts 56 are moved from the stack 74 until there are no more inserts in the insert receiver 70.

The lift 72 includes a riser that supports the stack 74 from the bottom. The lift 72 includes a prime mover, such as an electric motor or any other suitable device, that moves the riser up and down relative to the insert receiver 70. In the illustrated embodiment, the riser is a conveyor (e.g., a lift conveyor). The lift conveyor is configured to move a stack 74 of lower inserts 56 to position the stack on the lift 72 (from the insert conveyor 82 described below). In the illustrated embodiment, the lift conveyor includes a conveyor belt, which moves the stack.

The insert supplier 68 includes one or more keepers 76. The keepers 76 ensure that only one lower insert 56 is removed at a time by the insert transporter 66. In the illustrated embodiment, the insert supplier 68 includes a keeper 76 on each side of the insert receiver 70. Each keeper 76 is configured to engage the subsequent upper-most lower insert 56 in the stack 74 to retain or keep said lower insert in the insert receiver 70 when the top or upper-most lower insert is removed by the insert transporter 66. As illustrated, the lower inserts 56 in the stack 74 are nested together, such that they may stick together. In this case, the keepers 76 engage the subsequent upper-most lower insert 56 in the stack 74 as the upper-most lower insert is removed from the insert receiver 70 by the insert transporter 66 to prevent the subsequent upper-most lower insert that is stuck to the upper-most lower insert from being removed with the upper-most lower insert. Each keeper 76 is moveable between a keeping position and a non-keeping position. In the keeping position, the keeper 76 is positioned to engage (or be engaged by) the subsequent upper-most lower insert 56 in the stack 74. This way the keeper 76 retains the subsequent upper-most lower insert 56 in the stack 74. In the non-keeping position, the keeper 76 is positioned to not engage (or to not be engaged) by the stack 74 of lower inserts 56 when the lift 72 raises the stack of lower inserts to move the upper-most insert (formerly the subsequent upper-most insert) to the removal location. Each keeper 76 is operatively connected to a prime mover, such as a linear piston or electric motor, that moves the keeper between the keeping and non-keeping positions.

The insert supplier 68 includes an insert sensor 78. The insert sensor 78 is configured to detect the presence of a lower insert 56 in the removal location of the insert receiver 70. The insert sensor 78 may be any suitable sensor for detecting the presence of the lower insert 56 such as but not limited to a proximity sensor (e.g., a photoelectric sensor, infrared sensor). The insert sensor 78 is generally aligned (e.g., coplanar) with the removal location.

The insert supplier 68 also includes an orientation sensor 80. The orientation sensor 80 is configured to detect the orientation of the lower insert 56 at the removal location. If the lower insert 56 is in the incorrect orientation as detected by the orientation sensor 80, then the insert transporter 66 will rotate (about 180 degrees) the lower insert to the proper orientation before placing the lower insert in the box (e.g., when moving the lower insert into to the box).

The insert supplier 68 includes an insert conveyor 82. The insert conveyor 82 is configured to move additional or subsequent stacks 74 of lower inserts 56 toward the lift 72.

The insert conveyor 82 allows additional stacks 74 of lower inserts 56 to be staged so that once the stack on the lift 72 is gone, the lift 72 can return to a loading position where the lift is arranged to receive the next stack from the insert conveyor. For example, the riser receives the stack from the insert conveyor 82. The conveyor of the riser may also operate (e.g., move) in cooperation with the insert conveyor 82 to position the stack on the lift 72. In the illustrated embodiment, the insert conveyor 82 comprises a plurality of individual conveyors arranged end to end. Each individual conveyor is independently moveable of the other individual conveyors. For example, each individual conveyor has its own prime mover, such as an electric motor, that is operatively coupled to a conveyor belt. Each individual conveyor also includes an insert sensor, such as the insert sensor described above, for detecting whether a stack 74 of lower inserts 56 is present on that individual conveyor. Being able to individually move sections of the insert conveyor 82 allows stacks 74 to be placed on the insert conveyor 82 at generally any time, instead of all at once (when empty) as would be the case if the insert conveyor included only one moveable section instead of multiple moveable sections.

The insert supplier 68 may also include two guide walls 84 at the entry to the insert conveyor 82. The guide walls 84 are on opposite sides of the insert conveyor 82. The guide walls 84 are arranged to engage the sides of a stack 74 of lower inserts 56 if the stack is leaning too far to one side or the other to straight or true up the stack. By straightening the stack 74, the likelihood of the stack falling over while on the insert conveyor 82 is reduced and the stack is properly arranged to be moved into the insert receiver 70.

The lower insert placer 64 may include a box sensor (not shown), such as a photo eye, configured to detect the presence of a box B on the carriage 50. This can be used to confirm there is in fact a box B on the carriage 50 before placing lower insert 56 (e.g., prevents the lower insert from being placed on a carriage with no box).

The lower insert placer 64 may include an insert placer controller (not shown) for controlling the operations of the lower insert placer. The insert placer controller may be a dedicated controller for the lower insert placer 64 or a controller of the system 10. The insert placer controller controls the insert transporter 66 and the insert suppliers 68. The insert placer controller includes a CPU or process (e.g., an insert placer processor) and RAM or memory (broadly, non-transitory computer readable storage medium). Broadly, the memory includes (e.g., stores) processor-executable instructions for controlling the operation of the lower insert placer 64 and the components thereof. The instructions embody one or more of the functional aspects of the lower insert placer 64 and the components thereof (as described herein), with the processor executing the instructions to perform said one or more functional aspects. The components of the lower insert placer 64 may be in wired or wireless communication with the insert placer controller. Other control configurations are within the scope of the present disclosure.

The insert placer controller is communicatively coupled to the lift 72 (e.g., prime mover thereof). The insert placer controller is configured to operate each lift 72 to move the lower inserts 56 upward toward the removal location after the upper-most lower insert of the stack 74 has been removed from the removal location to move the subsequent upper-most lower insert to the removal location. The insert placer controller is communicatively coupled to each insert sensor 78. The insert placer controller operates the lift 72 based on information or signals received from the corresponding insert sensor 78. The insert placer controller is configured to operate the lift 72 (e.g., prime mover) to move the corresponding lower inserts 56 upward when the insert sensor 78 does not detect the presence of the lower insert in the removal location until the insert sensor detects the presence of a lower insert (e.g., subsequent upper-most lower insert). When a lower insert 56 (e.g., upper-most lower insert) is in the removal location, the insert sensor 78 detects the presence of the lower insert and informs (e.g., sends a signal to) the insert placer controller accordingly. Once the upper-most lower insert 56 is removed from the removal location, by the insert transporter 66, the insert sensor 78 no longer detects a lower insert in the removal location and informs the insert placer controller. The insert placer controller then operates the lift 72 to raise the riser and the stack 74 of lower inserts 56 until the subsequent upper-most lower insert is positioned at the removal location. Once the subsequent upper-most lower insert 56 enters the removal location, its presence is detected by the insert sensor 78, which informs the insert placer controller. Upon receiving the signal from the insert sensor 78 that a lower insert 56 is now in the removal location, the insert placer controller stops the movement of the lift 72. Accordingly, the insert placer controller generally conducts a closed loop process or routine to repeatedly move the stack 74 of lower inserts 56 upward to replace the lower insert removed from the removal location.

A similar closed-loop process can be used to move the stacks 74 of lower inserts 56 on the insert conveyor 82 toward the insert receiver 70. Using the insert sensors on each individual conveyor of the insert conveyor 82, the insert placer controller can operate the individual conveyors such that the stacks 74 are staged one after another adjacent the insert conveyor. For example, if the insert sensor of the individual conveyor adjacent the insert receiver 70 does not detect a stack 74 but another insert sensor of another individual conveyor does, the insert placer controller can operate the necessary individual conveyors to move the stack to the individual conveyor adjacent the insert receiver.

The insert placer controller can also operate the insert transporter 66 to rotate the lower insert 56 if needed. For example, the insert placer controller can receive a signal from the orientation sensor 80 that the lower insert 56 is in the incorrect orientation. Based on this signal, the insert placer controller can operate the insert transporter 66 such that the insert transporter rotates the lower insert after the insert transporter picks up the lower insert.

After the lower insert 56 is placed in the box B, the carriage 50 supporting the box travels (downstream) along the pathway 48 to move the box to the syringe station 16.

Figure 10:
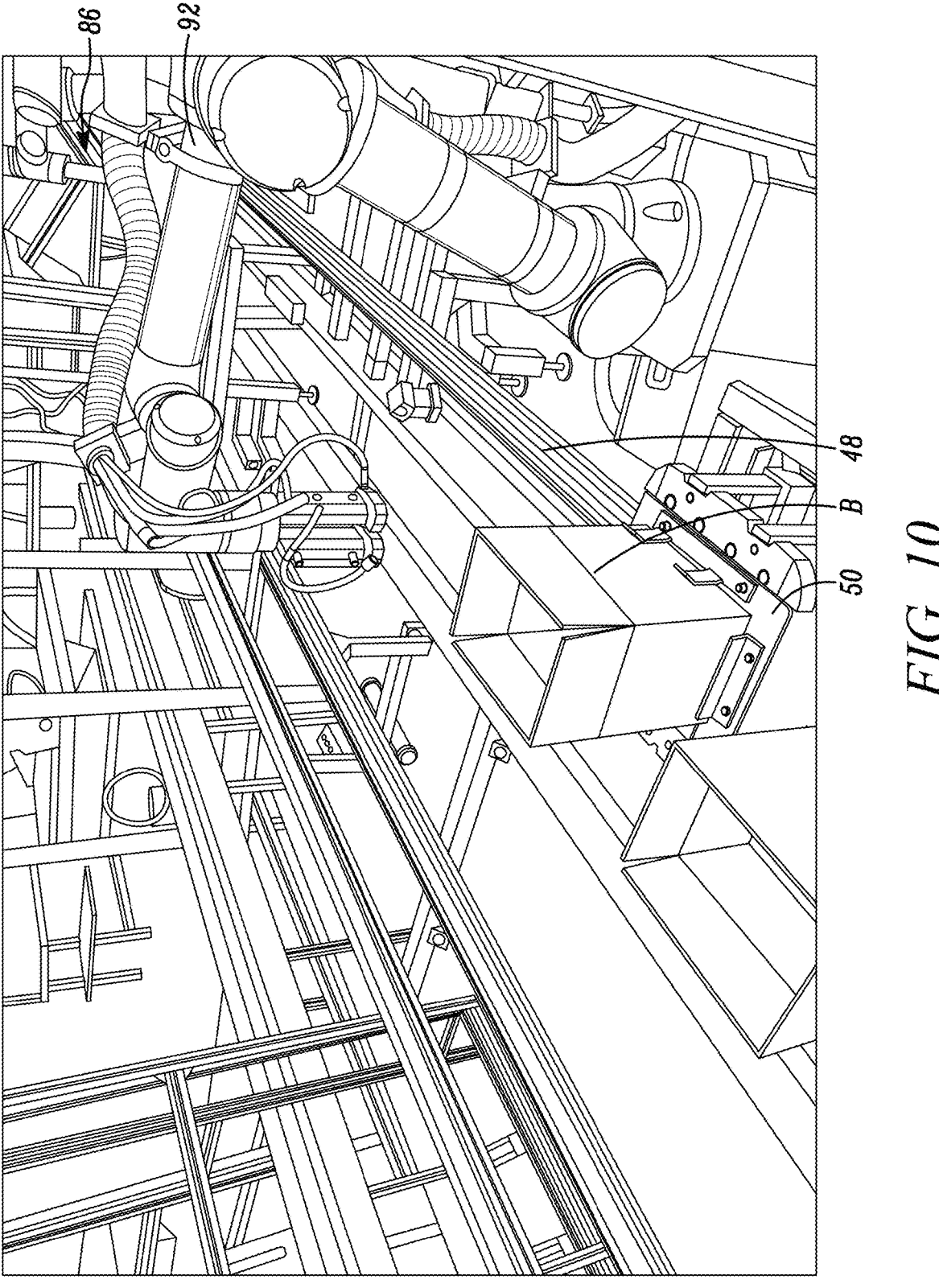
FIG. 10 is a perspective of a syringe placer of the pharmaceutical order processing system.
Figure 11:
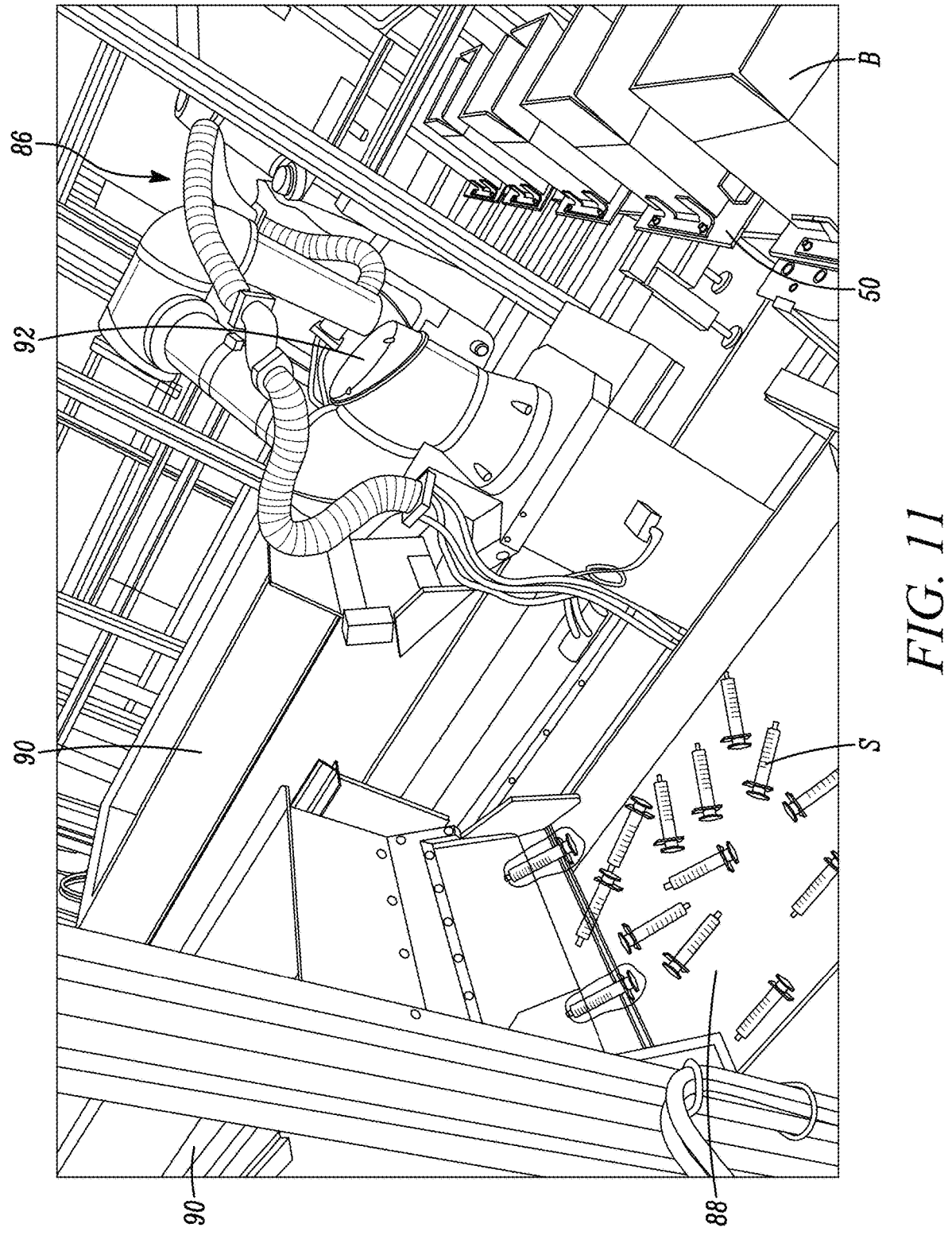
FIG. 11 is a perspective of the syringe placer.
Figure 12:
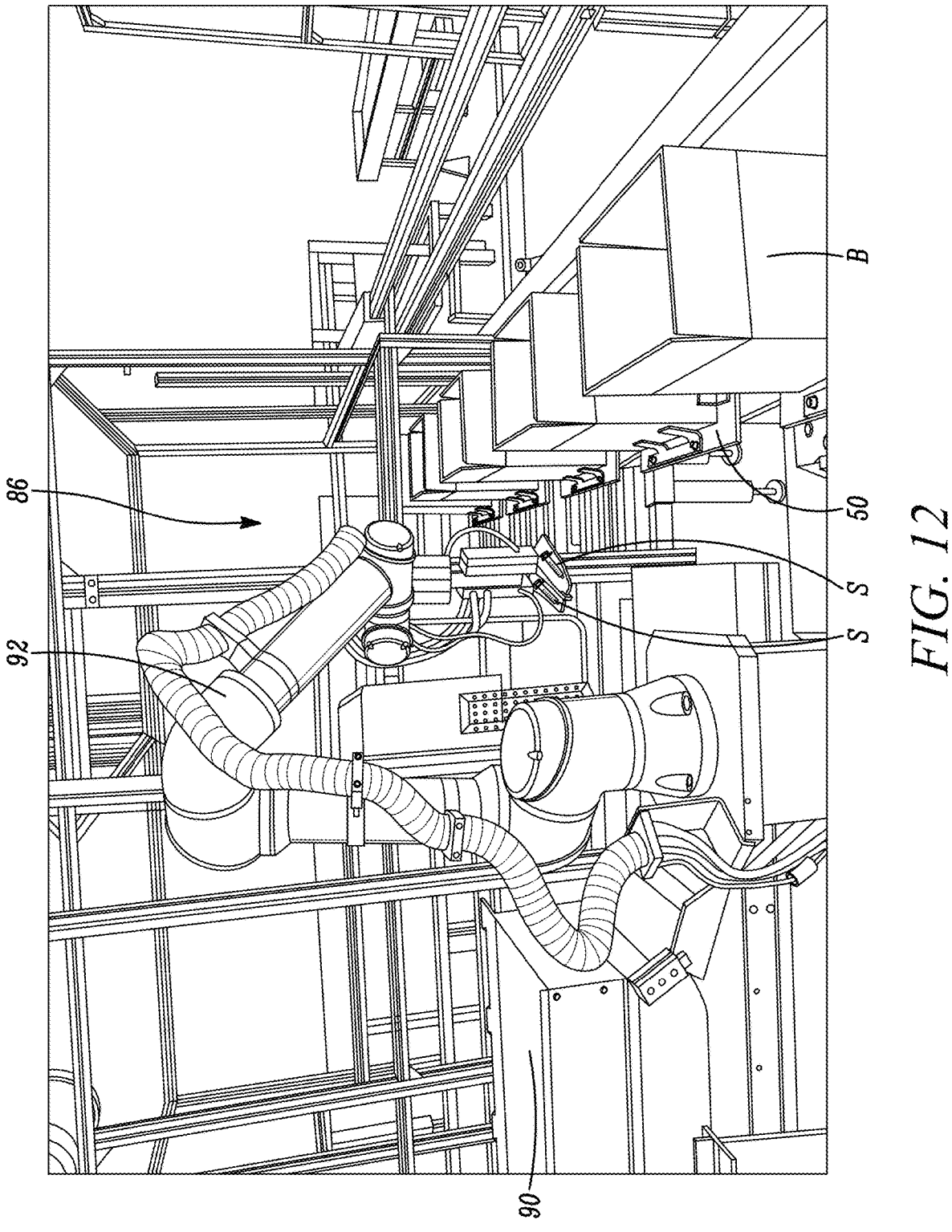
FIG. 12 is a perspective of the syringe placer.

Referring to FIGS. 10-12, the syringe station 16 includes a syringe placer 86. The syringe placer 86 is configured to place a syringe S into the syringe compartment 58 of the lower insert 56 (broadly, place the syringe in the box B). The syringe placer 86 includes a shaker table 88 with a hopper 90 and a syringe transporter 92. The hopper 90 holds a supply of syringes S, which are moved onto and spread out over the shaker table 88 via the shaking. In the illustrated embodiment, the syringe placer 86 includes two shaker tables 88 with hoppers 90, one on each side of the syringe transporter 92. This provides redundancy, enabling the syringe placer 86 to still be able to place the syringes S into boxes B even if one of the shaker tables 88 stops working. The two shaker tables 88 with hoppers 90 are generally identical. The syringe transporter 92 is configured to pick up and remove the syringes S from the table 88 and place the syringes in the box B. In the illustrated embodiment, the syringe transporter 92 comprises a robot such as a six-axis robotic arm, although other robots are within the scope of the present disclosure. For example, the syringe transporter 92 may comprise a selective-compliance-articulated robotic arm, a cylindrical robot, a delta robot, a polar coordinate robot, a vertically articulated robot, a Cartesian coordinate robot or any other suitable device. The syringe transporter 92 includes a syringe grabber (broadly, end-of-arm tooling) configured to selectively grab one or more syringes S to move the syringes. The syringe grabber may be configured to pick up one, or preferably more than one (e.g., two), syringes S at a time. A camera system (not shown) detects the position of the syringes S on the shaker table 88 and the syringe transporter 92 grabs the syringes S off the shaker table based on the detected position. The shaker table 88 is preferably stationary (e.g., not shaking) when the syringe transporter 92 grabs the syringes S. Other configurations are within the scope of the present disclosure. After the one or more syringes S are placed in the box B, the carriage 50 supporting the box travels (downstream) along the pathway 48 to move the box to the dosing cup station 18.

Figure 13:
FIG. 13 is a perspective of a dosing cup placer of the pharmaceutical order processing system.
Figure 14:
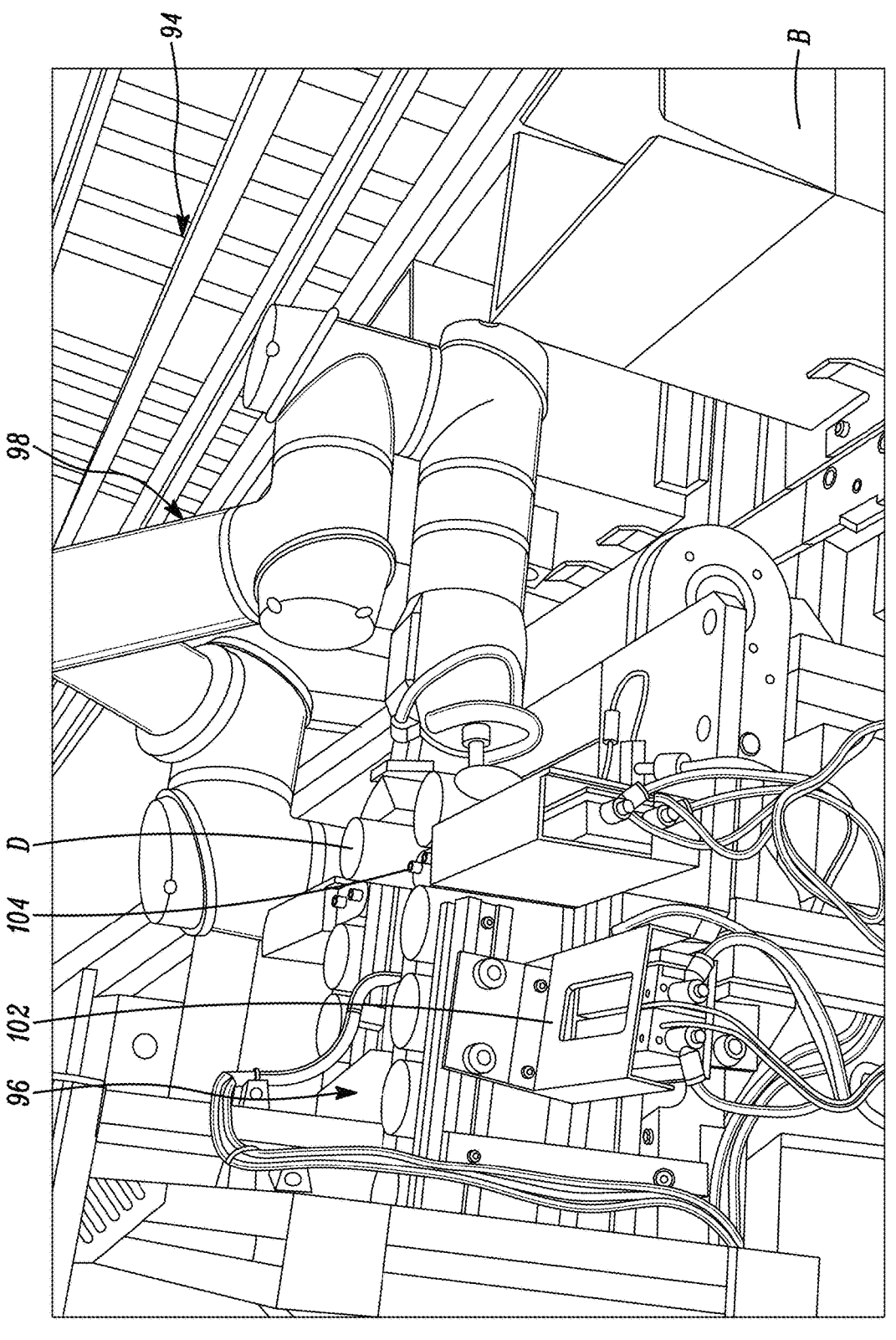
FIG. 14 is a perspective of the dosing cup placer.

Referring to FIGS. 13 and 14, the dosing cup station 18 includes a dosing cup placer 94. The dosing cup placer 94 is configured to place a dosing cup D into the dosing cup compartment 60 of the lower insert 56 (broadly, place the dosing cup in the box B). In the illustrated embodiment, the dosing cup placer 94 is configured to place two dosing cups D into the box B as the same time. The dosing cup placer 94 includes a dosing cup singulator 96 and a dosing cup transporter 98. The dosing cup transporter 98 is configured to pick up and remove the dosing cups D from the dosing cup singulator 96 and place the dosing cups in the box B. In the illustrated embodiment, the dosing cup transporter 98 comprises a robot such as a six-axis robotic arm, although other robots are within the scope of the present disclosure. For example, the dosing cup transporter 98 may comprise a selective-compliance-articulated robotic arm, a cylindrical robot, a delta robot, a polar coordinate robot, a vertically articulated robot, a Cartesian coordinate robot or any other suitable device. The dosing cup transporter 98 includes a dosing cup grabber (broadly, end-of-arm tooling) configured to selectively grab one or more dosing cups D to move the dosing cups. The dosing cup grabber may be configured to pick up one, or preferably more than one (e.g., two), dosing cups D at a time. In the illustrated embodiment, the dosing cup grabber includes two suction cups, each suction cup arranged to pick up one dosing cup D from the dosing cup singulator 96.

The dosing cup singulator 96 is configured to singulate or individualize a plurality of dosing cups D and position the singulated dosing cups in a position to be grabbed (and subsequently moved) by the dosing cup transporter 98. Because the dosing cup transporter 98 picks up two dosing cups D at once, the dosing cup singulator 96 includes two singulator lines 100. Each singulator line 100 singulates one of the dosing cups D picked up by the dosing cup transporter 98. Each singulator line 100 defines a pickup position at the end thereof. The two pickup positions are spaced apart by the same distance as the suction cups on the dosing cup transporter 98 (which is also the same distance between the dosing cup compartments 60 in the lower insert 56 are spaced apart). The two singulator lines 100 are generally identical, so one will now be described with the understanding the description applies to both singulator lines. The singulator line 100 includes opposite first and second rails defining a dosing cup channel therebetween sized and shaped to guide the dosing cups D in a single-file line. The base of the channel is defined by a conveyor (e.g., conveyor belt) which moves the dosing cups within the channel toward the pickup position. It is appreciated that the same conveyor underlies both channels of the two singulator lines 100. Immediately proceeding the pickup position are first and second stops 102, 104. Each stop 102, 104 is configured to contact or engage one dosing cup D to inhibit the dosing cups from moving with the conveyor. The stops 102, 104 are independently controllable. The each stop 102, 104 can be extended into the channel to engage the dosing cups D and retracted from the channel to permit the dosing cups to pass the respective stops. Each stop 102, 104 is operatively coupled to a prime mover, such as a linear actuator, to move the stops between the extended and retracted positions. To singulate a dosing cup D, the first stop 102 is retracted and the second stop 104 is extended. The conveyor is operated until the lead dosing cup D contacts the second stop. After, the first stop 102 is extended. The first stop 102 is positioned such that it engages the next subsequent dosing cup D after the lead dosing cup. With the first stop 102 extended, the second stop 104 retracts and the conveyor is operated to move the lead dosing cup to the pickup position. A stop (e.g., stationary or fixed stop) engages the lead dosing cup D to position the lead dosing cup in the pickup position. While the conveyor is moving the lead dosing cup D to the pickup position, the first stop 102 remains extended preventing the subsequent dosing cup and all the dosing cups after it from moving with the conveyor. After the lead dosing cup D is in the pickup position, the lead dosing cup D is picked up by the dosing cup transporter 98. In one embodiment, the second stop 104 may extend after the lead dosing cup D is in the pickup position but before the lead dosing cup is picked up to act as a brace against which the dosing cup transporter 98 can push the lead dosing cup so that the suction cup grips the lead dosing cup. After the lead dosing cup D is removed from the pickup position, the second stop 104 extends (or remains extended). The first stop 102 then retracts and the conveyor is operated to move the new lead dosing cup toward the second stop 104, allowing the process to repeat for the next dosing cup D.

The dosing cups may be automatically or manually loaded into the respective singulator lines 100. In one embodiment, the dosing cup station 18 may include a capper which automatically applies a cap to each container of the dosing cup D before the dosing cups are placed in the dosing cup singulator 96.

After the one or more dosing cups D are placed in the box B, the carriage 50 supporting the box travels (downstream) along the pathway 48 to move the box to the box check station 20. After the dosing cup station 18 but before the box check station 20, the pathway 48 includes a first branch or return loop 48A which allows the carriage 50 to return back to the erector station 12 or lower insert station 14. For example, should the box B on the carriage 50 not be properly filled with the lower insert 56, the syringes S and/or the dosing cups D (as determined at the box check station), the carriage 50 can return back to be properly filled. The first return loop 48A also allows the carriages 50 to bypass the lower insert station 14, the syringe station 16 and the dosing cup station 18 should one or more of these stations be out of order.

The box check station 20 includes a workplace for an operator to manually check to make sure each box B has received the lower insert 56, the syringes S and the dosing cups D. The workplace also allows the operator to manually insert one or more of the lower insert 56, the syringes S and the dosing cups D should one or more of the lower insert station 14, the syringe station 16 and/or the dosing cup station 18 be out of order. Most often, the carriage 50 will move right through the box check station to the pharmaceutical container station 22.

Figure 15:
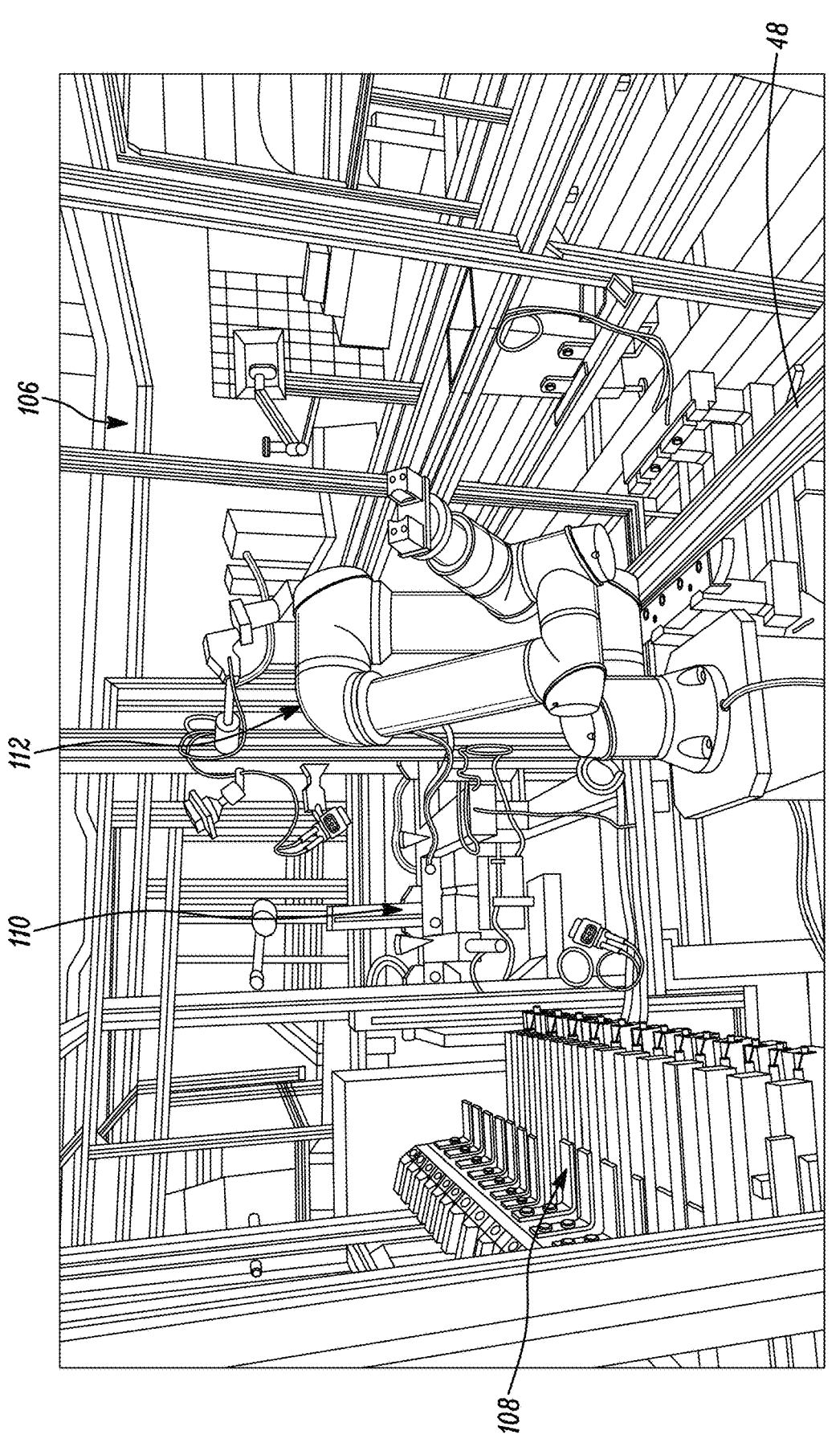
FIG. 15 is a perspective of a pharmaceutical container processing system of the pharmaceutical order processing system.
Figure 16:
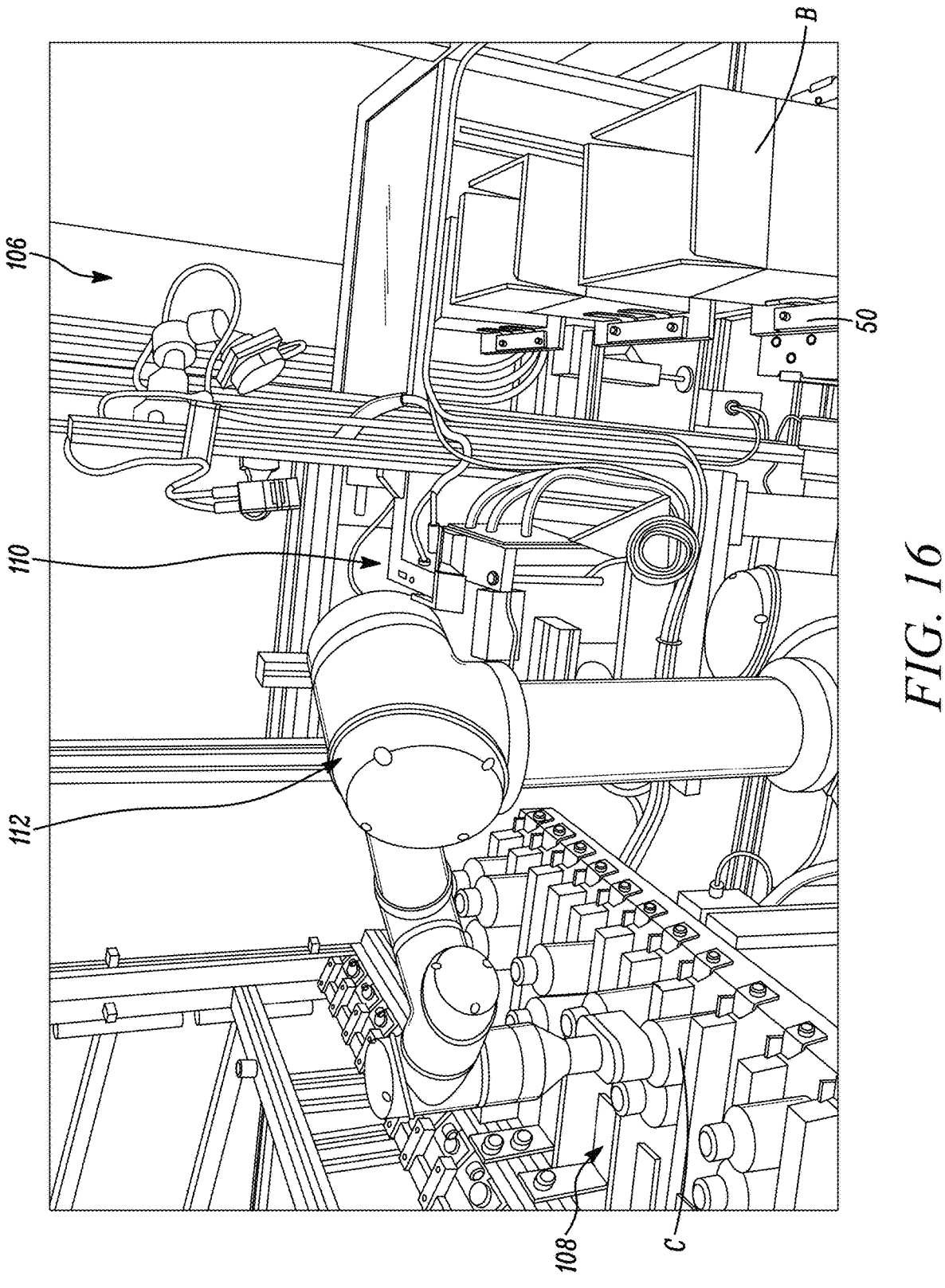
FIG. 16 is a perspective of the pharmaceutical container processing system.

Referring to FIGS. 15 and 16, the pharmaceutical container station 22 includes a pharmaceutical container placer 106 (broadly, a pharmaceutical container processing system). In the illustrated embodiment, the pharmaceutical container station 22 includes three pharmaceutical container placers 106. The three pharmaceutical container placers 106 are generally identical. The pathway 48 includes branch paths 48B for each pharmaceutical container placer 106. Each branch path 48B takes the carriages 50 off the main path and to one of the pharmaceutical container placers 106 and then back to the main path. One pharmaceutical container placer 106 will now be described with the understanding its description applies to all the pharmaceutical container placers.

The pharmaceutical container placer 106 is configured to place a pharmaceutical container C into a pharmaceutical container compartment 62 of the lower insert 56 (broadly, in the box B). The pharmaceutical container placer 106 includes a container repository 108, a labeler 110, and a container transporter 112. The container repository 108 receives and holds the pharmaceutical containers C and can hold many different types of pharmaceutical containers. The container repository 108 can be configured to hold pharmaceutical containers C of different shapes and of generally any size. For example, the container repository 108 can be configured for round bottles and square bottles, and any combination thereof. In one embodiment, the pharmaceutical containers C are manually loaded onto (e.g., into) the container repository 108 by an operator. The container repository 108 includes a plurality of channels sized and shaped so that the pharmaceutical containers C are arranged one after another (e.g., single file) in the channel. The container repository 108 includes a conveyor (e.g., conveyor belt) underlying the channels that moves the pharmaceutical containers C along the channels and to a pick up location where the pharmaceutical containers are picked up by the container transporter 112.

The container transporter 112 is configured to pick up and remove a pharmaceutical container C from the container repository 108 and place the pharmaceutical container in the box B. The container transporter 112 picks up a pharmaceutical container C that container the specific type of pharmaceutical needed to fill the prescription order. In the illustrated embodiment, the container transporter 112 comprises a robot such as a six-axis robotic arm, although other robots are within the scope of the present disclosure. For example, the container transporter 112 may comprise a selective-compliance-articulated robotic arm, a cylindrical robot, a delta robot, a polar coordinate robot, a vertically articulated robot, a Cartesian coordinate robot or any other suitable device. The container transporter 102 includes a container grabber (broadly, end-of-arm tooling) configured to selectively grab a pharmaceutical container C to move the pharmaceutical container.

The container transporter 112 moves the pharmaceutical container C past (e.g., along) the labeler 110 as the pharmaceutical container moves from the container repository 108 to the box B. The labeler 110 is configured to apply a label (e.g., a patient specific label) to the pharmaceutical container C. In one embodiment, the labeler 110 may print and then apply the label to the pharmaceutical container C. Labelers are generally known in the art, and thus a further description of the labeler is omitted herein. For example, the labeler 110 may be a pass through labeler that applies the label to the pharmaceutical container C as the container is moved through the labeler by another component. In this embodiment, the container transporter 112 moves the pharmaceutical container C to and along (e.g., through) the labeler 110. As the container transporter 112 moves the pharmaceutical container C along the labeler 110, the labeler applies the patient specific label to the container C (generally over the existing manufacturer's label). In one embodiment, the pharmaceutical container placer 106 may include a first identification scanner to scan the pharmaceutical container C before the label is applied to confirm the right container has been selected and a second identification scanner to scan the pharmaceutical container C after the label is applied to confirm the right label was applied and/or properly applied. Further details on pharmaceutical placers may be found in U.S. Provisional Patent Application No. 63/273,002, the entirety of which is incorporated herein by reference. For example, in one embodiment the pharmaceutical container placer of the present disclosure includes the systems and methods described in U.S. Provisional Patent Application No. 63/273,002 for re-labeling container, or more specifically for applying the patient specific label to the pharmaceutical container over the manufacturer's label in such a manner as to leave the existing gap between the side edges of the manufacture's label to permit a patient to look through the gap and container body to view the interior contents of the container.

In one embodiment, the pharmaceutical container placer 106 picks the pharmaceutical container C and generates (e.g., prints) the patient specific label based off the identifier(s) from the machine-readable marking on the box B and/or the identification tag on the carriage 50. For example, in one embodiment, a scanner of the pharmaceutical container placer 106 obtains the identifier from the machine-readable marking on the box B or the identification tag on the carriage 50. The container transporter 112 then picks the pharmaceutical container C from the container repository 108 that is corresponds to the pharmaceutical order associated with the identifier. Similarly, the labeler 110 prints a label that corresponds to the pharmaceutical order associated with the identifier. In one embodiment, the pharmaceutical container placer 106 includes two scanners, one that obtains the identifier from the machine-readable marking on the box B and another that obtains the identifier from the identification tag on the carriage 50. The pharmaceutical container placer 106 may then compare the two identifiers to make sure the correct box B is still being supported by the correct carriage 50 (e.g., to make sure the box has not been removed and placed on a different carriage). Other stations may also obtain both identifiers to perform this verification as well.

After the one or more pharmaceutical containers C are placed in the box B (by one or more pharmaceutical container placers 106), the carriage 50 supporting the box travels (downstream) along the pathway 48 to move the box to the manual stations 26. At this stage, the box B is filled with the lower insert 56, the syringes S, the dosing cups D, and one or more pharmaceutical containers C as generally shown in FIG. 4. After the pharmaceutical container station 18 but before the first manual station 26, the pathway 48 includes a second branch or return loop 48C, which allows the carriage 50 to return back to the pharmaceutical container station 22. This allows a carriage 50 and corresponding box B to make multiple trips through the pharmaceutical container station 22 (e.g., visit other pharmaceutical container placers 106) should additional pharmaceutical containers C need to be placed in the box to fill the prescription order.

Figure 17:
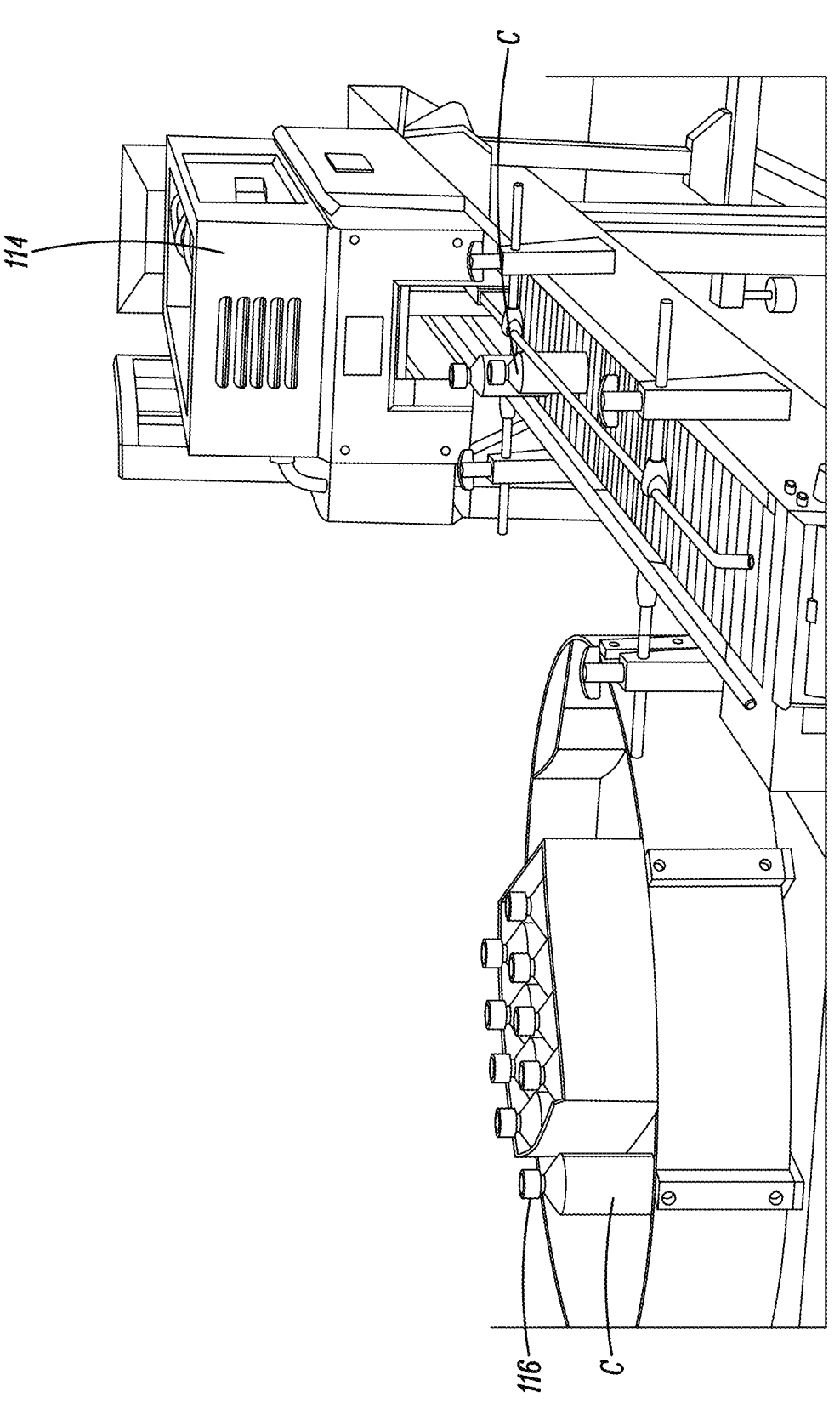
FIG. 17 is a perspective of a heat shrink sealer of the pharmaceutical container processing system.

Referring to FIG. 17, related to the pharmaceutical container station 22, the system 10 may include a filling station 24 (e.g., manual filling station). To the extent required, the manual filling station 24 allows workers to manually fill pharmaceutical containers C with the prescription before the pharmaceutical container C is placed on the container repository 108. It is understood not all pharmaceutical containers C will be manually filled at the filling station 24. For instance, some pharmaceutical containers C come from the manufacturer with the right amount of the prescription as mentioned above and these containers will not need to be manually filled before being placed on the container repository 108. For the pharmaceutical containers C that do need to be manually filled, the filling station 24 includes a workplace (e.g., tabletop) and a heat shrink sealer 114 for applying a heat shrink seal 116 around the cap of the manually filled pharmaceutical container.

Figure 18:
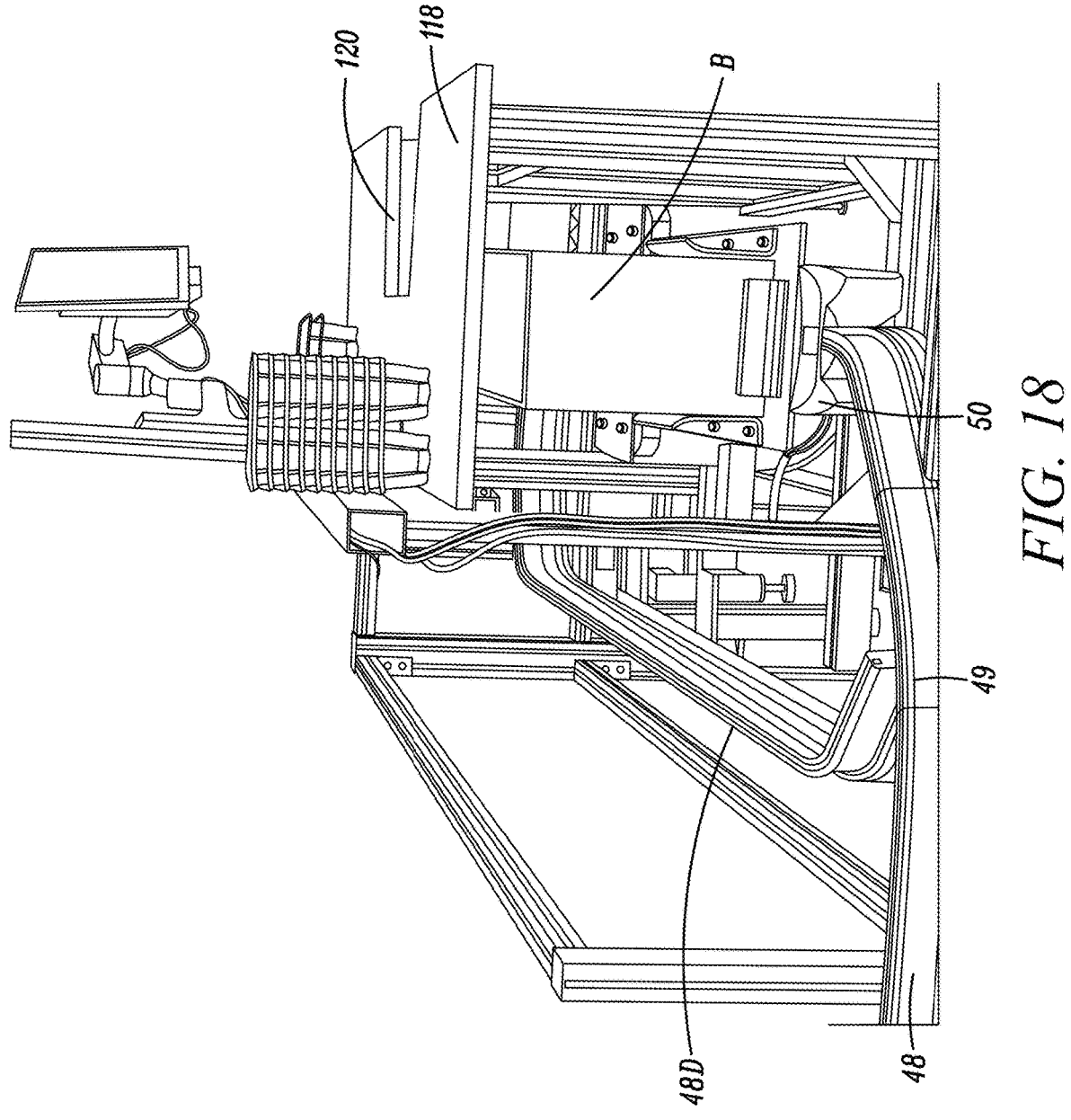
FIG. 18 is a perspective of a manual station of the pharmaceutical container processing system.
Figure 19:
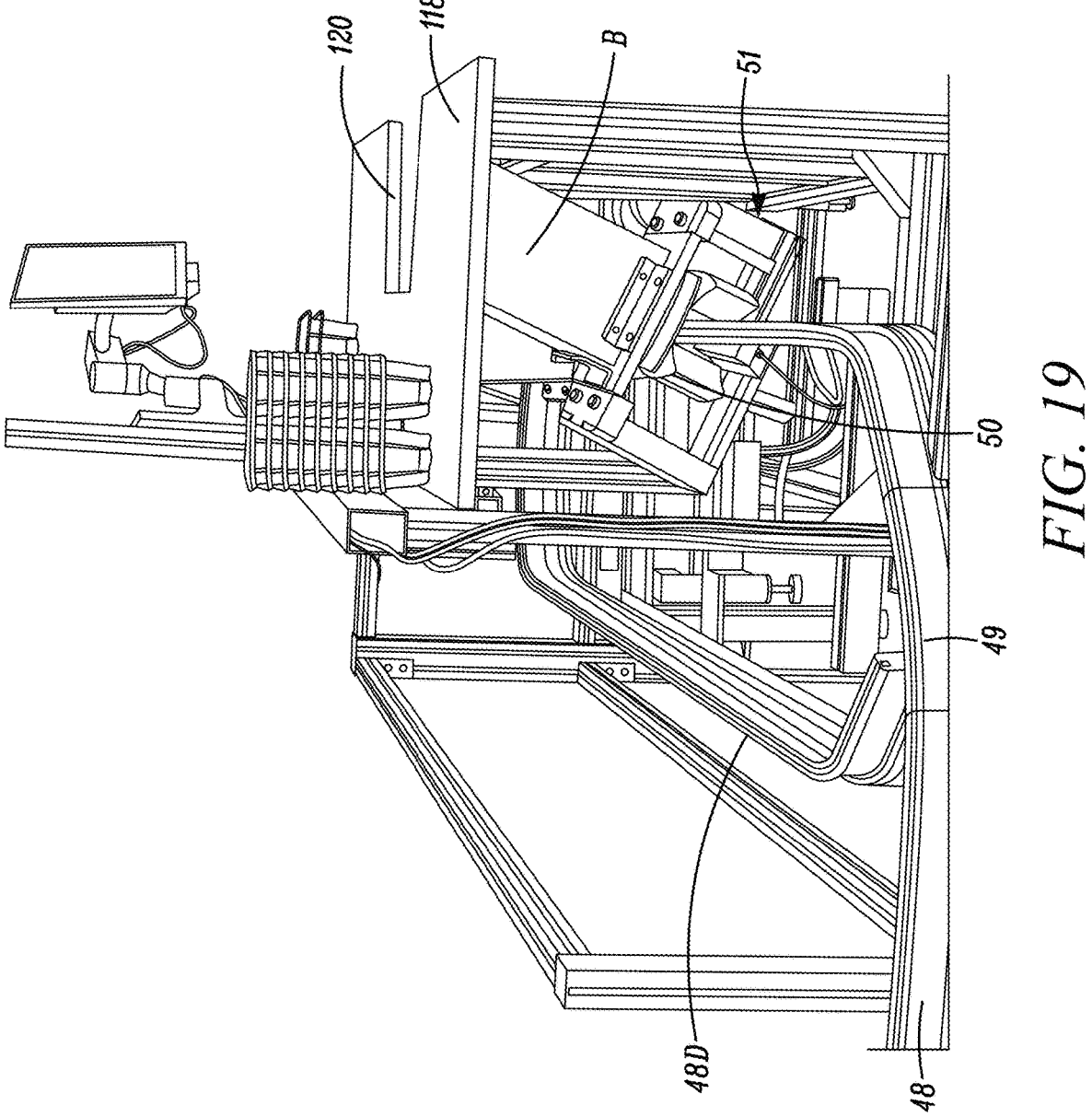
FIG. 19 is a perspective of the manual station.

Referring to FIGS. 3, 18 and 19, the system 10 may include a plurality of manual stations 26. In the illustrated embodiment, the system 10 includes five manual stations 26. Each manual station 26 may include a table 118 for an operator to work at. The pathway 48 includes a manual station branch path 48D that extends under the table 118. The pathway 48 includes a connector segment or switch 49 that rotates between different three different positions: one position connects the main path to the upstream end of the manual station branch path 48D to allow carriages to move onto the manual station branch path; a second position (shown in FIGS. 18 and 19) connects the main path to the downstream end of the manual station branch path to allow carriage to move off the manual station branch path and back onto the main path; and a third position allows the carriage to bypass the manual station branch path and remain on the main path. The table 118 defines a box opening 120 arranged to align with a box B on a carriage 50 when the carriage stops at a position along the manual station branch path 48D of the pathway 48. As shown in FIG. 19, the manual station branch path 48D may include a tilter configured to tilt the carriage 50 and box B supported thereby at an angle, such as about 30 degrees from vertical, to make it easier for an operator (such as a pharmacist) to look into and access the box though the box opening 120. In the illustrated embodiment, the tilter is part of the carriage holder 51. Other configurations of the tilter are within the scope of the present disclosure.

The manual stations 26 allows different manual tasks to performed. For example, referring to FIG. 3, in the illustrated embodiment, there are four different tasks performed across the manual stations 26. It is understood each manual station 26 can perform any of the tasks, but that generally each manual station with only perform one of the tasks at a time. One manual station 26A can be used to manually place a pharmaceutical container C in the box B. Another manual station 26B can be used to add first time patient information and literature and/or additional syringes S and dosing cups D. Another manual station 26c can be used to manually correct any errors that occur along the system 10 (e.g., a pharmaceutical container C was placed in the wrong box B). Another manual station 26D can be used by a pharmacist to manually verify the pharmaceutical container C placed in the box B is the correct container for the corresponding patient's prescription order. In the illustrated embodiment, there are two manual stations 26D. It is understood other tasks may be performed at the manual stations.

After the manual stations 26, the carriage 50 supporting the box B travels (downstream) along the pathway 48 to move the box to the upper insert station 28. After the manual stations 26 but before the upper insert station 28, the pathway 48 includes a third branch or return loop 48E which allows the carriage 50 to return back to one or more of the manual stations 26. This allows a carriage 50 and corresponding box B to make multiple trips through the manual stations 26. For example, if a pharmacist at one of the verification manual stations 26D determines an error occurred, the carriage 50 can be directed to the manual correction manual station 26c via the third return loop 48E in order to be manually corrected.

Figure 20:
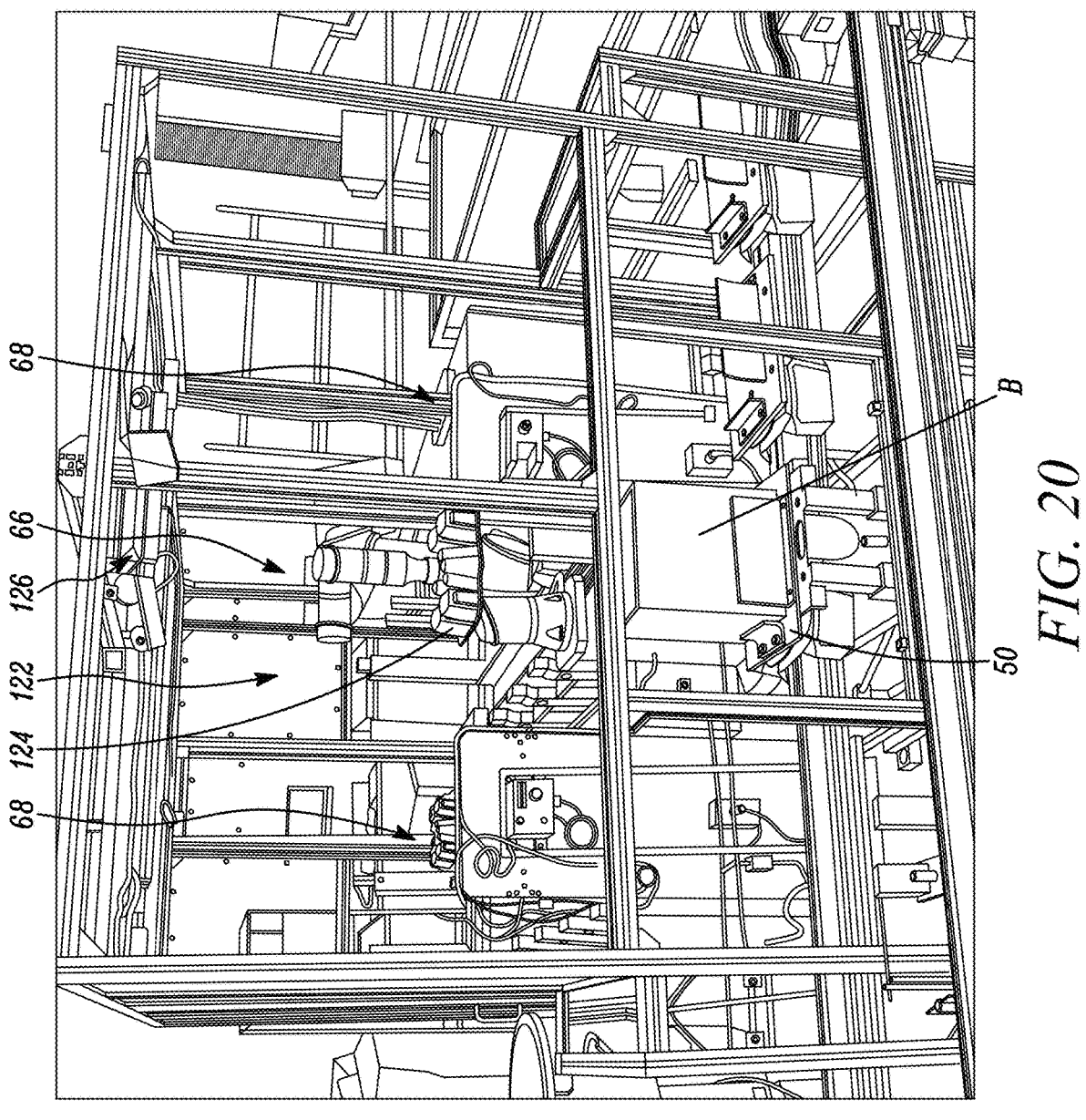
FIG. 20 is a perspective of an upper insert placer of the pharmaceutical order processing system.

Referring to FIG. 20, the upper insert station 28 includes an upper insert placer 122. The upper insert placer 122 is configured to place an upper insert 124 into the box B (when the carriage 50 carrying the box is at the upper insert station 28). When placed in the box B, the upper insert 124 generally encloses the elements (e.g., syringes S, dosing cups D, pharmaceutical container(s) C) placed in the lower insert 56. The upper insert 124 may include one or more syringe compartments, one or more dosing cup compartments and/or one or more pharmaceutical container compartments that align with the corresponding compartments of the lower insert 56 when the upper insert is inserted into the box B to surround and enclose the elements in the compartments. The upper insert placer 122 is generally identical to the lower insert placer 64, and thus like reference numerals are used to indicate like components. Accordingly, the above descriptions regarding the lower insert placer 64 also apply to the upper insert placer 122. For example, the upper insert placer 122 includes an insert transporter 66 configured to move the upper insert 124 into the box B. The main difference between the upper insert placer 122 and the lower insert placer 64 is that the upper insert grabber (broadly, end-of-arm tooling) of the insert transporter 66 configured to selectively grab an upper insert 124 instead of a lower insert 56. In one embodiment, the upper insert station 28 may include a camera 126 arranged to be positioned above the box B and the carriage 50 to take a picture of the inside of the box (e.g., the syringes S, the dosing cups D and the pharmaceutical container(s) C) for record keeping purposes before the upper insert 124 is inserted into the box.

Figure 6:
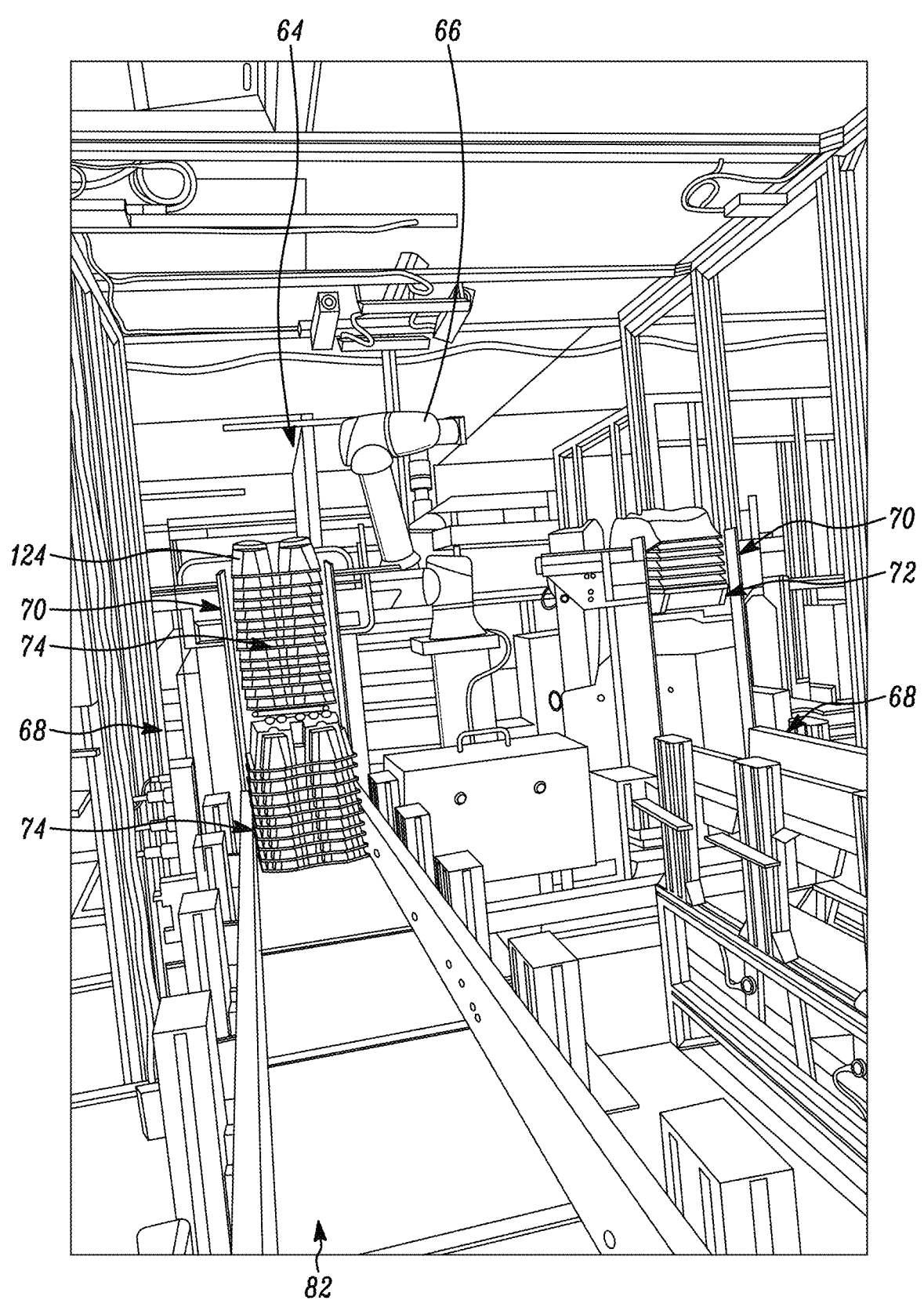
FIG. 6 is a perspective of insert supply lines of the lower insert placer.
Figure 7:
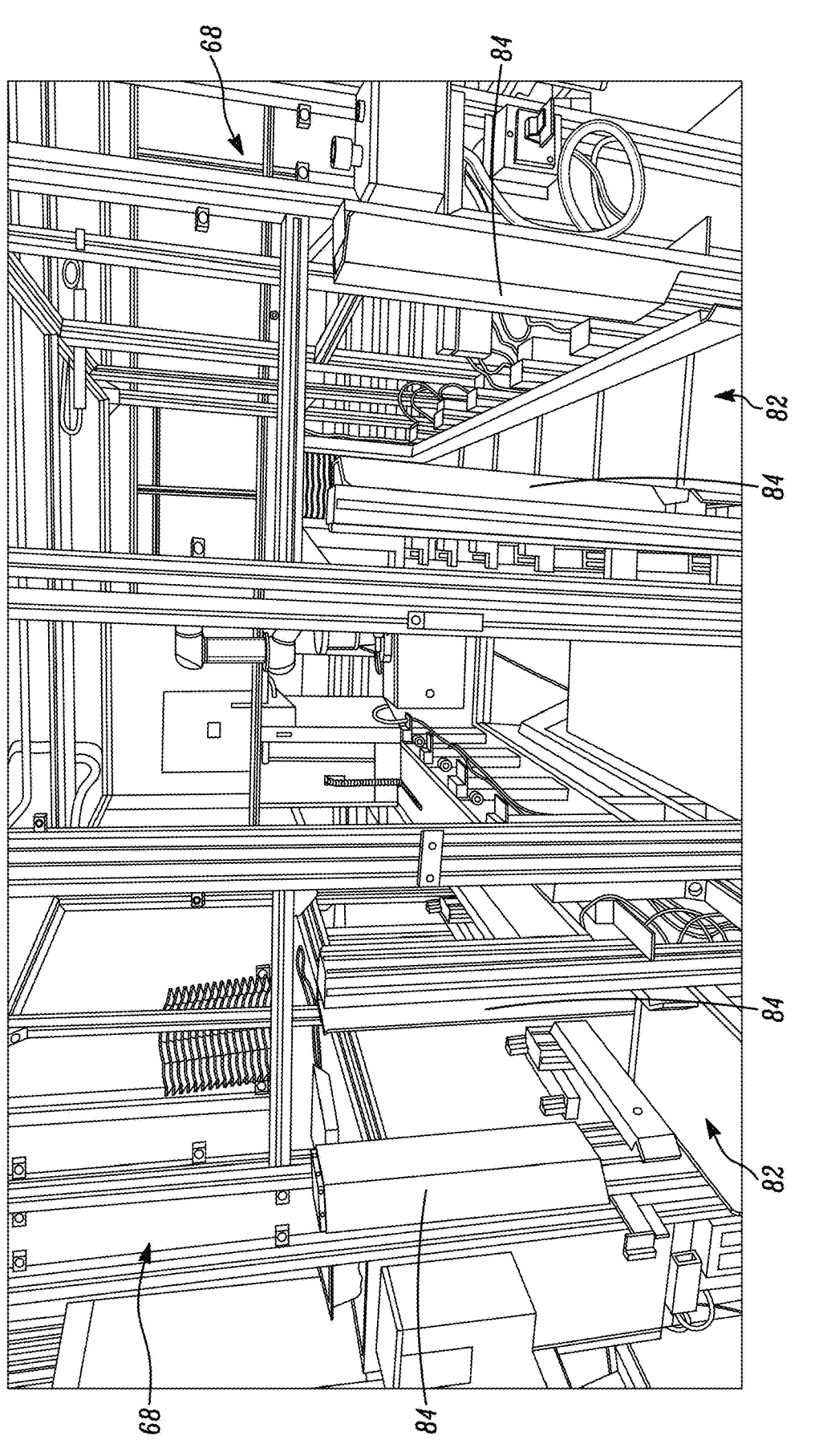
FIG. 7 is a perspective of the insert supply lines.
Figure 8:
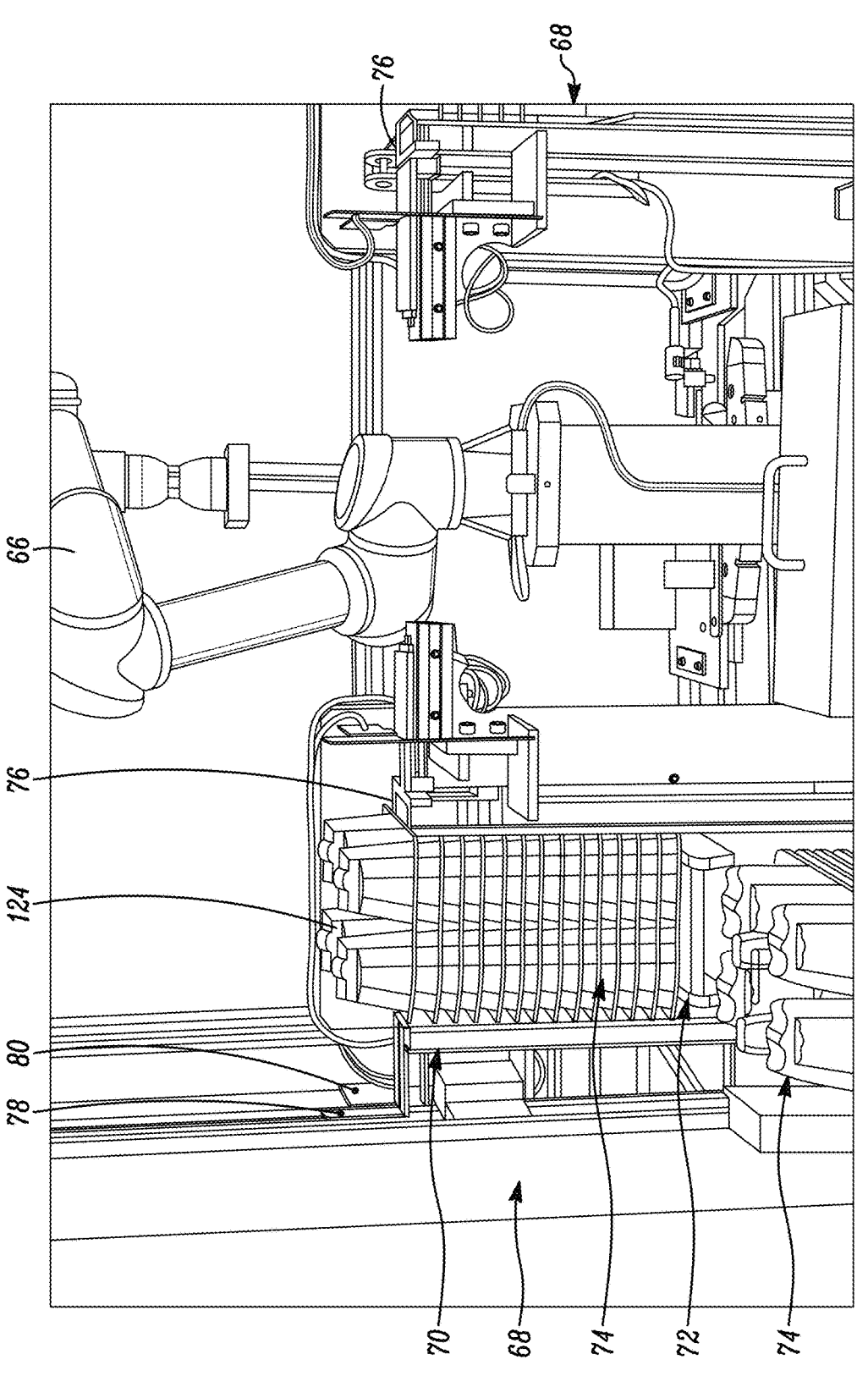
FIG. 8 is an enlarged perspective of the insert supply line.
Figure 9:
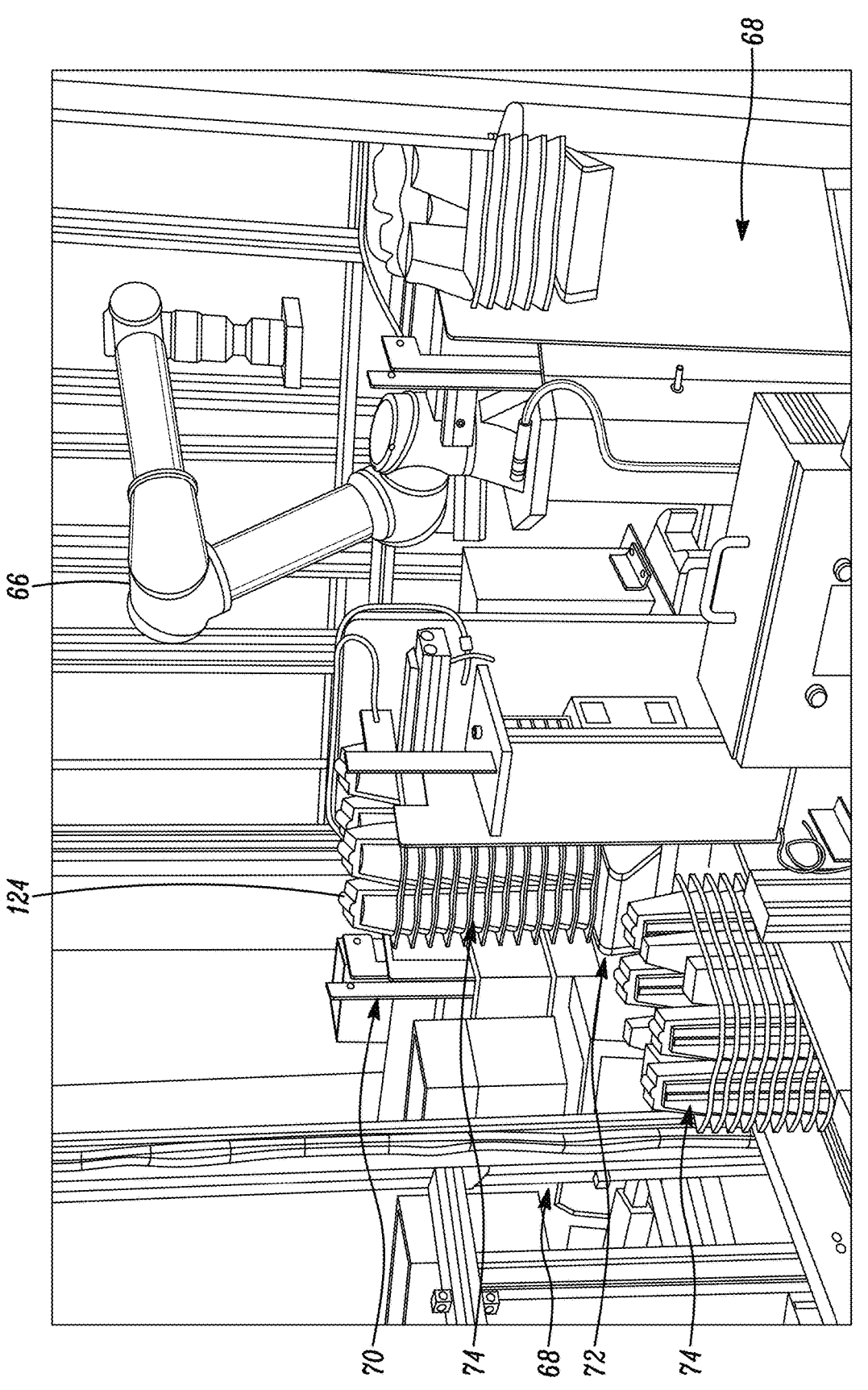
FIG. 9 is an enlarged perspective of the insert supply line.

It is appreciated that FIGS. 6, 8 and 9 that were referred to during the discussion regarding the lower insert placer 64 show upper inserts 124. However, since the lower and upper insert placers 64, 122 are generally identical, it is understood that the placers are constructed and operate in generally the same way. Accordingly, when discussing the construction and operations of the lower and upper insert placers 64, 122, references to the lower and upper inserts 56, 124 are generally interchangeable.

After the upper insert 124 is placed in the box B, the carriage 50 supporting the box travels (downstream) along the pathway 48 to move the box to the manual paper insert station 30 and automatic paper insert station 32.

Referring back to FIGS. 1-3, the system 10 includes a manual paper insert station 30 and an automatic paper insert station 32. The system 10 may include either the manual paper insert station 30 or the automatic paper insert station 32. The manual paper insert station 30 may include one or more printers that print literature (e.g., prescription instructions, etc.) associated with the prescription order corresponding to the box B. An operator can then take the printed literature and place it in the box B. In one embodiment, the printers print the literature in response to the scanning (manually or automated), using a scanner, the machine-readable marking on the box B and/or the identification tag of the carriage 50. The printers print the literature corresponding to the prescription order associated with the identifier. The automatic paper insert station 32 includes printers and a literature placer that places the printed literature from the printers in the box B. The automatic paper insert station 32 may also include a scanner that obtains the identifier(s) from the machine-readable marking and/or identification tag to print the literature, as described above. It is understood the carriage 50 and its box B would generally stop at only one of the manual paper insert station 30 or the automatic paper insert station 32, although in some embodiments the carriage and box may stop at both. Other ways of adding the literature to the box B are within the scope of the present disclosure.

Other configurations of the manual paper insert station 30 and the automatic paper insert station 32 are within the scope of the present disclosure. For example, with reference to FIGS. 21 and 22, in one embodiment of the system 10 the pathway 48 includes one or more branch paths that takes the carriages 50 off the main path, to the manual paper insert station 30 and/or the automatic paper insert station 32, and then back to the main path. In the illustrated embodiment, the manual paper insert station 30 is configured like the manual stations 26 (as described herein). In other words, in this embodiment, the manual paper insert station 30 is just another type of manual station 26. The manual paper insert station 30 may include the branch path 48D, the table 118, the tilter, and the printers as described above. In the illustrated embodiment, the automatic paper insert station 32 includes an automatic paper insert branch path 48G. The upstream end of the automatic paper insert branch path 48G is connected to the branch path 48D of the manual paper inset station 30 and the downstream end of the automatic paper insert branch path is connected to the main path of the pathway 48. The automatic paper insert branch path 48G takes the carriages 50 to (e.g., by) the literature placer to receive the literature therefrom. In one embodiment, the system 10 includes a scanner along the main path of the pathway 48, upstream of the manual paper insert station 30 and the automatic paper insert station 32, that scans the machine-readable marking on the box B and/or the identification tag of the carriage 50. After scanning, the system 10 can then determine whether the box should go to the manual paper insert station 30 and/or the automatic paper insert station 32, and set the corresponding switches accordingly to direct the carriage to the manual paper insert station and/or the automatic paper insert station. This scanner can also be used obtain the identifiers used to print the literature as described above.

After the literature is placed in the box B at the manual paper insert station 30 and/or the automatic paper insert station 32, the carriage 50 supporting the box travels (downstream) along the pathway 48 to move the box to the weight station 34.

The weight station 34 includes a scale that weights the box B. The actual weight of the box B as measured by the scale is compared against a predicted weight generated based on the prescription order. The predicted weight is generated by adding the predicted weight of the box and each element that is supposed to be contained therein (e.g., syringes S, dosing cups D, one or more pharmaceutical containers C, literature, etc.) based on the prescription order. If the actual weight is too different from the predicted weight (e.g., outside a predicted weight range), the system 10 flags the box B and the carriage 50 supporting the box is redirected to the manual correction manual station 26c via a fourth return loop 48F and the third return loop 48E in order to be manually inspected and corrected if needed. The fourth return loop 48F connects with the third return loop 48E and the main pathway upstream of the upper insert station 28.

After the box B passes the weight inspection at the weight station 34, the carriage 50 supporting the box travels (downstream) along the pathway 48 to move the box to the unloading station 36.

At the unloading station, the box B is removed from the carriage 50. This may be done manually or automatically with a box transporter. The box transporter can comprise a robot such as a six-axis robotic arm, although other robots are within the scope of the present disclosure. For example, the box transporter may comprise a selective-compliance-articulated robotic arm, a cylindrical robot, a delta robot, a polar coordinate robot, a vertically articulated robot, a Cartesian coordinate robot or any other suitable device. The box transporter includes a box grabber (broadly, end-of-arm tooling) configured to selectively grab the box B to move the box. At this point, the carriage 50 and the box B diverge from each other. The carriage 50, now empty, returns along the main path of the pathway 48 to the erection station 12 to receive a new box B to repeat the process. The box B, unloaded from the carriage 50, is moved to the box closing station 38.

The box closing station 38 includes a box closer 128 that receives the box B from the unloading station. The box closer 128 is configured to close the box B. The box closer 128, as generally known in the art, may fold the upper flaps of the box B down and tap them shut to close the box.

The system 10 includes a box conveyor 130 that carries the box B from the box closing station 38 to the shipping label station 40. The shipping label station 40 may include a printer that prints the shipping label and a shipping label placer that places the printed shipping label on the box B. The shipping label may be created based off scanning the machine-readable marking on the box B in generally the same manner as described above with the creation of the literature. After the shipping label station 40, the box conveyor 130 continues to carry the box B to the shipping label verification station 42. The shipping label verification station 42 can include a scanner that scans the shipping label to confirm the shipping label is readable (e.g., no errors occurred when applying the shipping label to the box B). The shipping label verification station 42 may also scan, with the same or different scanner, the machine-readable marking to obtain the identifier to confirm the applied shipping label is on the correct box B. The box conveyor 130 then transports the box B to the collection station 44 where the box is ready to be shipped. For example, an operator may manually stack the box B on a shipping pallet. In another embodiment, the collection station 44 may include a palletizer that removes the box B from the box conveyor and stacks the box on a pallet.

The above mention process of the box B traveling from the erector station 12 to the collection station 44 repeats itself for each box (e.g., each prescription order) processed by the system 10. It is understood that the stations may be operating generally simultaneously. For example, the lower insert placer 64 can be placing a lower insert 56 in one box B while the pharmaceutical container placer 106 is placing a pharmaceutical container C in another box.

The system 10 may include a control system for controlling the operations and processes of the system as described herein. In one example, the control system includes a system controller (broadly, a computer) for controlling the operation of the system 10. The control system can be a pharmacy system controller, e.g., as shown and described in U.S. Pat.

Nos. 10,303,854 and 9,697,335, the entireties of which are hereby incorporated by reference. The controller systems and methods can control the components as described herein and dispense the pharmaceutical containers C (e.g., bottles of liquid medicines). The system controller (e.g., a pharmaceutical order processing system controller) controls and/or is in communication with the different components of the system 10, such as individual component controllers (e.g., the insert placer controller). The system controller includes a CPU or processor (e.g., a pharmaceutical order processing system processor) and RAM or memory (broadly, non-transitory computer-readable storage medium). Generally, the system controller controls and operates the various components (e.g., lower insert placer 64, conveyor 46, pharmaceutical placer 64, etc.) of the system 10. Broadly, the memory includes (e.g., stores) processor-executable instructions for controlling the operation of the system 10 and the components thereof. The instructions embody one or more of the functional aspects of the system 10 and the components thereof (as described herein), with the processor executing the instructions to perform said one or more functional aspects. The components of the system 10 may be in wired or wireless communication with the controller. Other configurations of the control system are within the scope of the present disclosure.

The presently described systems and methods to automate fulfilling a prescription order can be used in various production environments. Some of these environments are described in U.S. patent application Ser. Nos. 17/973,879 and 17/973,829, which are hereby incorporated by reference in their entireties. The present pharmaceutical order processing systems can be part of a product packaging systems and tracked in the load balancing system in these applications.

Various embodiments described herein can provide a small footprint automated pharmacy with different types of redundancy, e.g., multiple supply lines to a single robotic mover and workstations 26 that can be modified to different tasks. The workstations 26 can be assigned to perform the various tasks as described in U.S. patent application Ser. No. 17/973,879.

The carriages 50 on the pathway 48 can be tracked and controlled according to the disclosure in U.S. patent application Ser. No. 17/973,829.

Although described in connection with an exemplary computing system environment, embodiments of the aspects of the disclosure are operational with numerous other general purpose or special purpose computing system environments or configurations. The computing system environment is not intended to suggest any limitation as to the scope of use or functionality of any aspect of the disclosure. Moreover, the computing system environment should not be interpreted as having any dependency or requirement relating to any one or combination of components illustrated in the exemplary operating environment. Examples of well-known computing systems, environments, and/or configurations that may be suitable for use with aspects of the disclosure include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the aspects of the disclosure may be described in the general context of data and/or processor-executable instructions, such as program modules, stored one or more tangible, non-transitory storage media and executed by one or more processors or other devices. Generally, program modules include, but are not limited to, routines, programs, objects, components, and data structures that perform particular tasks or implement particular abstract data types. Aspects of the disclosure may also be practiced in distributed computing environments where tasks are performed by remote processing devices that are linked through a communications network. In a distributed computing environment, program modules may be located in both local and remote storage media including memory storage devices.

In operation, processors, computers and/or servers may execute the processor-executable instructions (e.g., software, firmware, and/or hardware) such as those illustrated herein to implement aspects of the disclosure.

Embodiments of the aspects of the disclosure may be implemented with processor-executable instructions. The processor-executable instructions may be organized into one or more processor-executable components or modules on a tangible processor readable storage medium. Aspects of the disclosure may be implemented with any number and organization of such components or modules. For example, aspects of the disclosure are not limited to the specific processor-executable instructions or the specific components or modules illustrated in the figures and described herein. Other embodiments of the aspects of the disclosure may include different processor-executable instructions or components having more or less functionality than illustrated and described herein.

The order of execution or performance of the operations in embodiments of the aspects of the disclosure illustrated and described herein is not essential, unless otherwise specified. That is, the operations may be performed in any order, unless otherwise specified, and embodiments of the aspects of the disclosure may include additional or fewer operations than those disclosed herein. For example, it is contemplated that executing or performing a particular operation before, contemporaneously with, or after another operation is within the scope of aspects of the disclosure.

The Title, Field, and Background are provided to help the reader quickly ascertain the nature of the technical disclosure. They are submitted with the understanding that they will not be used to interpret or limit the scope or meaning of the claims. They are provided to introduce a selection of concepts in simplified form that are further described in the Detailed Description. The Title, Field, and Background are not intended to identify key features or essential features of the claimed subject matter, nor is it intended to be used as an aid in determining the claimed subject matter.

When introducing elements of aspects of the disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the aspects of the disclosure are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the aspects of the disclosure by way of example and not by way of limitation. This description enables one skilled in the art to make and use the aspects of the disclosure, and describes several embodiments, adaptations, variations, alternatives and uses of the aspects of the disclosure, including what is presently believed to be the best mode of carrying out the aspects of the disclosure. Additionally, it is to be understood that the aspects of the disclosure is not limited in its application to the details of construction and the arrangement of components set forth in the description or illustrated in the drawings. The aspects of the disclosure are capable of other embodiments and of being practiced or carried out in various ways. Also, it will be understood that the phraseology and terminology used herein is for the purpose of description and should not be regarded as limiting.

Having described aspects of the disclosure in detail, it will be apparent that modifications and variations are possible without departing from the scope of aspects of the disclosure as defined in the appended claims. It is contemplated that various changes could be made in the above constructions, products, and methods without departing from the scope of aspects of the disclosure. In the preceding specification, various embodiments have been described with reference to the accompanying drawings. It will, however, be evident that various modifications and changes may be made thereto, and additional embodiments may be implemented, without departing from the broader scope of the aspects of the disclosure as set forth in the claims that follow. The specification and drawings are accordingly to be regarded in an illustrative rather than restrictive sense.

What is claimed is:

1. A pharmaceutical order processing system for filling a prescription order, the pharmaceutical order processing system comprising:
 a lower insert placer configured to place a lower insert into a box;
 a syringe placer configured to place a syringe into a syringe compartment of the lower insert;
 a dosing cup placer configured to place a dosing cup into a dosing cup compartment of the lower insert;
 a pharmaceutical container placer configured to place a pharmaceutical container into a pharmaceutical container compartment of the lower insert; and
 an upper insert placer configured to place an upper insert into the box after the box has received the lower insert and the lower insert has received the syringe, the dosing cup and the pharmaceutical container.

2. The pharmaceutical order processing system of claim 1, further comprising a pathway and a box carriage movable along the pathway, the pathway extending between the lower insert placer, the syringe placer, the dosing cup placer, the pharmaceutical container placer and the upper insert placer, the box carriage configured to support and move the box along the pathway to the lower insert placer, the syringe placer, the dosing cup placer, the pharmaceutical container placer and the upper insert placer.

3. The pharmaceutical order processing system of claim 1, wherein the syringe placer is located upstream of the dosing cup placer along the pathway such that the syringe placer places the syringe in the lower insert before the dosing cup placer places the dosing cup in the lower insert.

4. The pharmaceutical order processing system of claim 1, further comprising one or more manual stations, each manual station including a table defining a box opening arranged to align with the box when the box is at the manual station.

5. The pharmaceutical order processing system of claim 1, further comprising a box ID applier configured to apply a machine-readable marking to the box, the machine-readable marking representing an identifier associated with the prescription order received by the pharmaceutical order processing system.

6. The pharmaceutical order processing system of claim 1, wherein the dosing cup placer includes a dosing cup singulator and a dosing cup transporter, the dosing cup singulator being configured to singulate a plurality of dosing cups and the dosing cup transporter being configured to move a singulated dosing cup of the plurality of dosing cups.

7. The pharmaceutical order processing system of claim 1, further comprising:
 a box erector configured to erect the box; and
 a box closer configured to close the box after the lower insert, the syringe, the dosing cup, the pharmaceutical container and the upper insert have been placed in the box.

8. The pharmaceutical order processing system of claim 1, further comprising a lower insert supplier configured to supply the lower insert to the lower insert placer, the lower insert supplier including:
 a lower insert receiver having an interior sized and shaped to receive and hold a stack of lower inserts, the lower insert receiver having a first upper removal location from which each lower insert is is removed from the lower insert receiver; and
 a first lift configured to raise the stack of lower inserts disposed in the interior of the lower insert receiver upward to move an upper-most lower insert in the stack of lower inserts to the first upper removal location.

9. The pharmaceutical order processing system of claim 8, further comprising an upper insert supplier configured to supply the upper insert to the upper insert placer, the upper insert supplier including:
 a upper insert receiver having an interior sized and shaped to receive and hold a stack of upper inserts, the upper insert receiver having a second upper removal location from which each upper insert is removed from the upper insert receiver; and
 a second lift configured to raise the stack of upper inserts disposed in the interior of the upper insert receiver upward to move an upper-most upper insert in the stack of upper inserts to the second upper removal location.

10. The pharmaceutical order processing system of claim 8, further comprising an insert conveyor configured to move a subsequent stack of lower inserts toward the first lift, the first lift being moveable to a loading position in which the first lift is arranged to receive the subsequent stack of lower inserts from the insert conveyor.

11. The pharmaceutical order processing system of claim 10, wherein the first lift includes a lift conveyor configured to move the subsequent stack of lower inserts received from the insert conveyor to position the subsequent stack of lower inserts on the first lift.

12. The pharmaceutical order processing system of claim 8, further comprising a keeper configured to engage a subsequent upper-most lower insert to retain the subsequent upper-most lower insert in the lower insert receiver when the upper-most lower insert is removed from the first upper removal location.

13. The pharmaceutical order processing system of claim 12, wherein the keeper is moveable between a keeping position in which the keeper is positioned to engage the subsequent upper-most lower insert and a non-keeping position in which the keeper is positioned to not engage the stack of lower inserts when the first lift raises the stack of lower inserts to move the upper-most lower insert to the first upper removal location.

14. The pharmaceutical order processing system of claim 8, further comprising an orientation sensor configured to detect an orientation of the lower insert, the lower insert placer being configured to rotate the lower insert to a proper orientation when moving the lower insert into the box based on the orientation detected by the orientation sensor.

15. The pharmaceutical order processing system of claim 2, further comprising an automatic paper insert station adjacent to the pathway downstream from the upper insert placer and configured to place literature in the box.

16. The pharmaceutical order processing system of claim 15, further comprising a manual paper insert station adjacent to the pathway downstream from the upper insert placer, wherein the pathway is configured to place the box carriage supporting the box adjacent to the manual paper insert station to provide access to the box so that the box can receive literature.

17. A pharmaceutical order processing system for filling a prescription order, the pharmaceutical order processing system comprising:
    a pathway;
    a box carriage movable along the pathway to move a box;
    a lower insert placer configured to place a lower insert into the box;
    a syringe placer downstream of the lower insert placer and configured to place a syringe into a syringe compartment of the lower insert;
    a dosing cup placer downstream of the lower insert placer and configured to place a dosing cup into a dosing cup compartment of the lower insert;

a pharmaceutical container placer downstream of the lower insert placer and configured to place a pharmaceutical container into a pharmaceutical container compartment of the lower insert; and
    an upper insert placer configured to place an upper insert into the box after the box has received the lower insert and the lower insert has received the syringe, the dosing cup and the pharmaceutical container;
    wherein the box carriage is configured to support and move the box along the pathway to the lower insert placer, the syringe placer, the dosing cup placer, the pharmaceutical container placer and the upper insert placer.

18. The pharmaceutical order processing system of claim 17, wherein the syringe placer is located upstream of the dosing cup placer along the pathway such that the syringe placer places the syringe in the lower insert before the dosing cup placer places the dosing cup in the lower insert; and wherein the pharmaceutical order processing system further comprises one or more manual stations including a table defining a box opening arranged to align with the box when the box is at the one or more manual stations.

19. The pharmaceutical order processing system of claim 18, further comprising an automatic paper insert station adjacent to the pathway downstream from the upper insert placer and configured to place literature in the box.

20. The pharmaceutical order processing system of claim 19, further comprising a manual paper insert station adjacent to the pathway downstream from the upper insert placer, wherein the pathway is configured to place the box carriage supporting the box adjacent to the manual paper insert station to provide access to the box so that the box can receive literature.

* * * * *